(12) United States Patent
Gamache

(10) Patent No.: US 8,573,653 B2
(45) Date of Patent: Nov. 5, 2013

(54) FITTING COMPONENT, FERRULE AND NUT

(75) Inventor: Yves Gamache, Adstock (CA)

(73) Assignee: Mecanique Analytique Inc., Thetford-Mines, Quebec (CA)

(*) Notice: Subject to any disclaimer, the term of this patent is extended or adjusted under 35 U.S.C. 154(b) by 0 days.

(21) Appl. No.: 13/412,152

(22) Filed: Mar. 5, 2012

(65) Prior Publication Data
US 2012/0228872 A1 Sep. 13, 2012

Related U.S. Application Data

(60) Provisional application No. 61/450,184, filed on Mar. 8, 2011.

(51) Int. Cl.
F16L 19/06 (2006.01)

(52) U.S. Cl.
USPC .......................... 285/342; 285/353; 285/385

(58) Field of Classification Search
USPC ............. 285/342, 343, 353, 385, 384, 389; 210/198.2, 656
See application file for complete search history.

(56) References Cited

U.S. PATENT DOCUMENTS

| | | | | |
|---|---|---|---|---|
| 1,725,853 A * | 8/1929 | Crotty | ................ | 285/342 |
| 1,797,277 A | 3/1931 | Thomas | | |
| 1,883,273 A | 10/1932 | Zerk | | |
| 2,127,611 A * | 8/1938 | Mueller | ............ | 285/342 |
| 2,182,811 A * | 12/1939 | Kocher | ............ | 285/342 |
| 2,316,806 A * | 4/1943 | Parker | ............ | 285/342 |
| 2,330,841 A * | 10/1943 | Parker | ............ | 285/342 |
| 2,761,705 A * | 9/1956 | Kreidel | ............ | 285/384 |
| 3,007,721 A * | 11/1961 | Schmohl et al. | ........... | 285/342 |
| 3,011,807 A * | 12/1961 | Cowdrey | ............ | 285/342 |
| 3,069,188 A * | 12/1962 | Crawford | ............ | 285/342 |
| 3,255,521 A | 6/1966 | Callahan | | |
| 4,260,182 A | 4/1981 | Bruner | | |
| 5,217,261 A | 6/1993 | DeWitt | | |
| 5,308,122 A * | 5/1994 | Crawford et al. | ........... | 285/342 |
| 5,669,637 A | 9/1997 | Chitty et al. | | |
| 6,273,478 B1 | 8/2001 | Benett et al. | | |
| 6,851,729 B2 * | 2/2005 | Gibson | ............ | 285/342 |
| 7,316,777 B2 | 1/2008 | Loy | | |
| 7,416,225 B2 * | 8/2008 | Williams | ............ | 285/342 |
| 7,419,192 B2 | 9/2008 | Benoit et al. | | |
| 7,641,242 B2 * | 1/2010 | Van Pelt | ............ | 285/384 |

(Continued)

FOREIGN PATENT DOCUMENTS

WO 0116517 A1 3/2001
WO 0173338 A1 10/2001

Primary Examiner — David E Bochna
(74) Attorney, Agent, or Firm — SmithAmundsen LLC; Dennis S. Schell

(57) ABSTRACT

A fitting component for receiving a tube is provided. The tube has a tube end inserted through a ferrule, the portion of the tube end extending beyond the ferrule being called a pilot. The fitting component comprises a body including a cavity for receiving the tube end and the ferrule. The cavity is defined by an inner lateral wall and opens on an extremity of the body. The cavity includes a pilot receiving section and a channel connecting the cavity to another portion of the body. A radial annular flange is located at the interface of the pilot receiving section with the channel. The flange has an annular sealing lip protruding towards the cavity. The sealing lip is for forming a seal with a radial surface of the pilot, advantageously reducing dead volumes within the fitting component when in use.

19 Claims, 22 Drawing Sheets

(56) References Cited

U.S. PATENT DOCUMENTS

| | | |
|---|---|---|
| 7,677,602 B2 | 3/2010 | Benett et al. |
| 2006/0284419 A1* | 12/2006 | Williams et al. .............. 285/342 |
| 2007/0194567 A1* | 8/2007 | Pliassounov .................. 285/384 |
| 2008/0007048 A1* | 1/2008 | Benoit et al. .................. 285/247 |
| 2010/0133806 A1 | 6/2010 | Barnett et al. |

\* cited by examiner

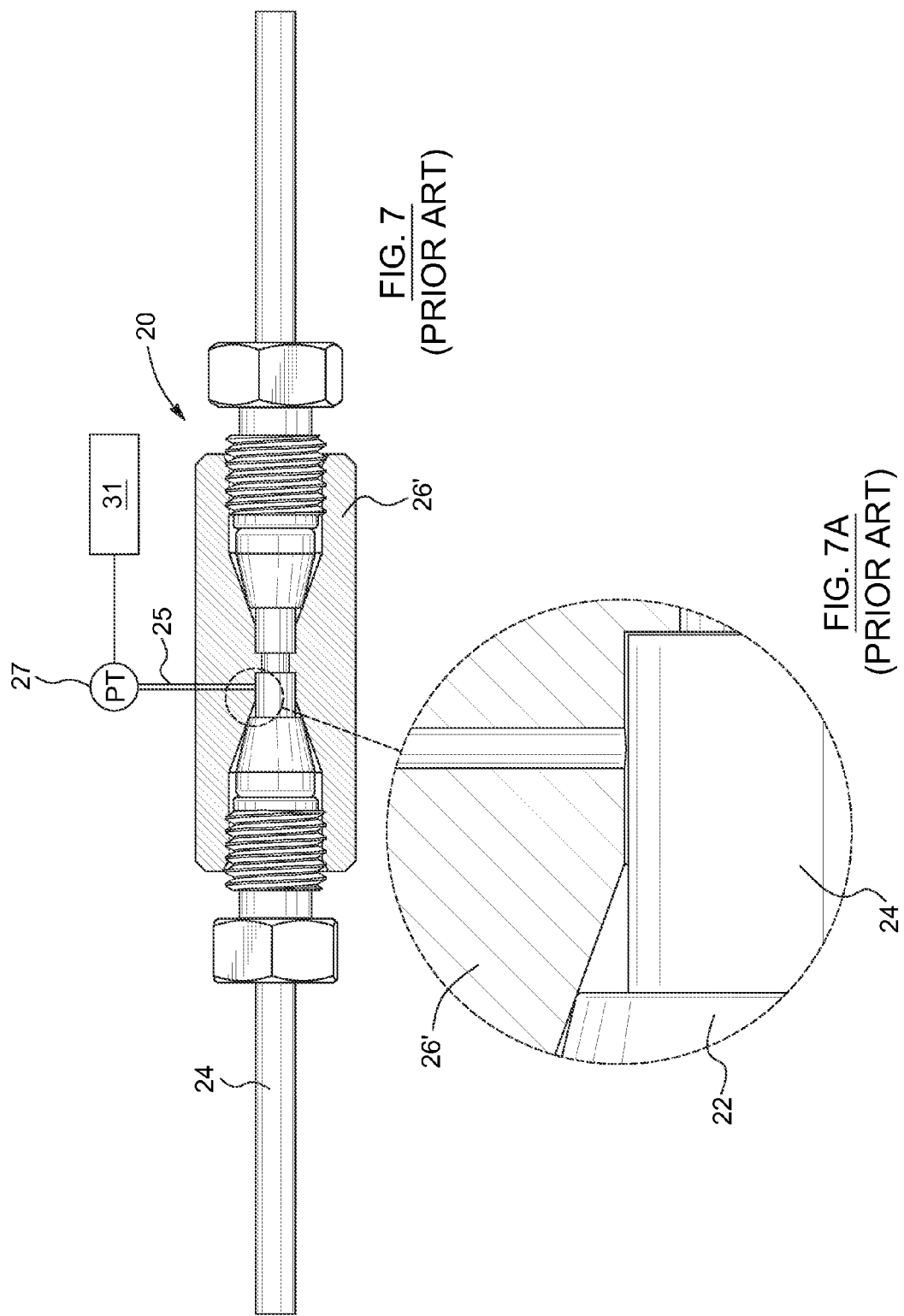

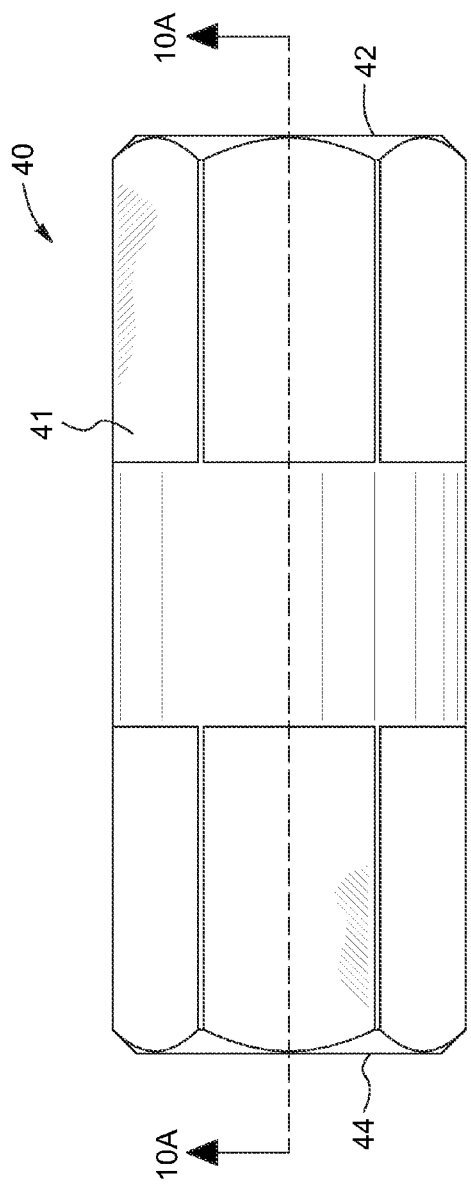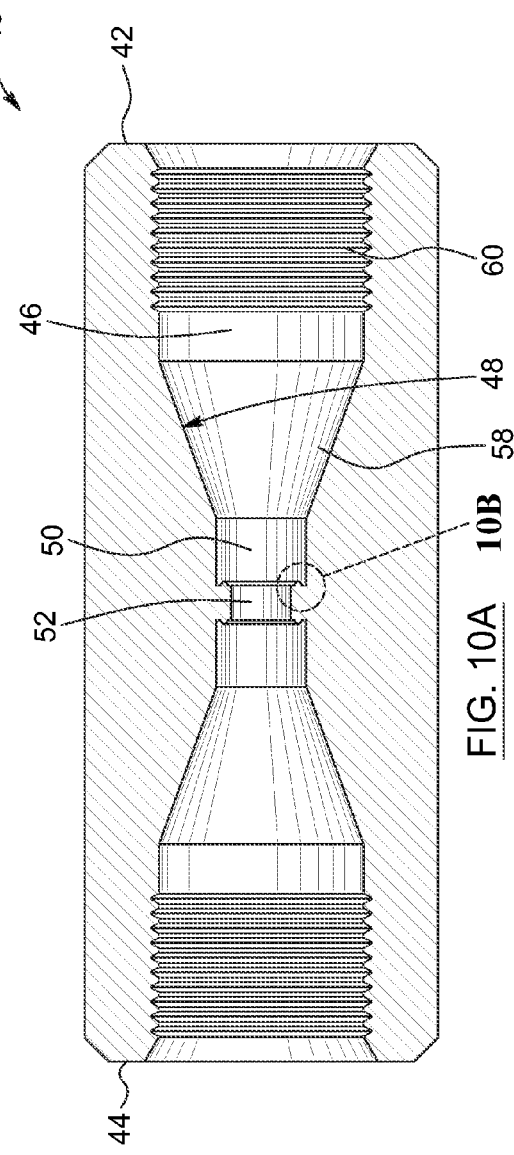

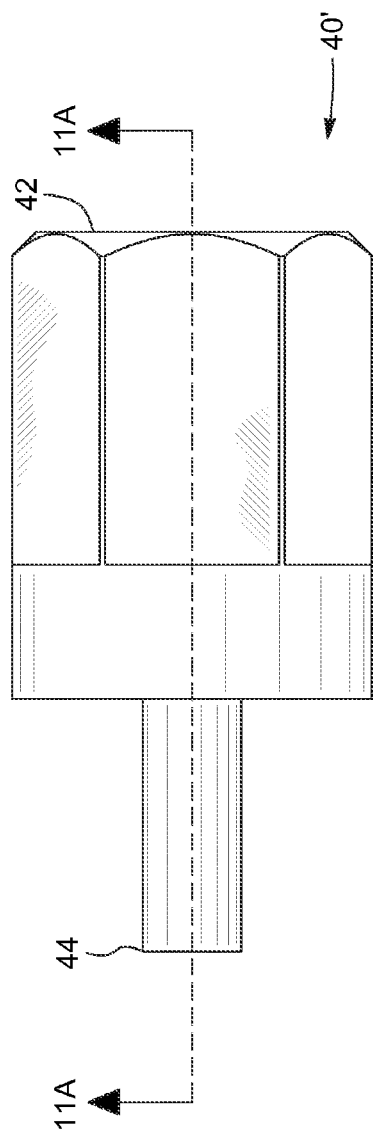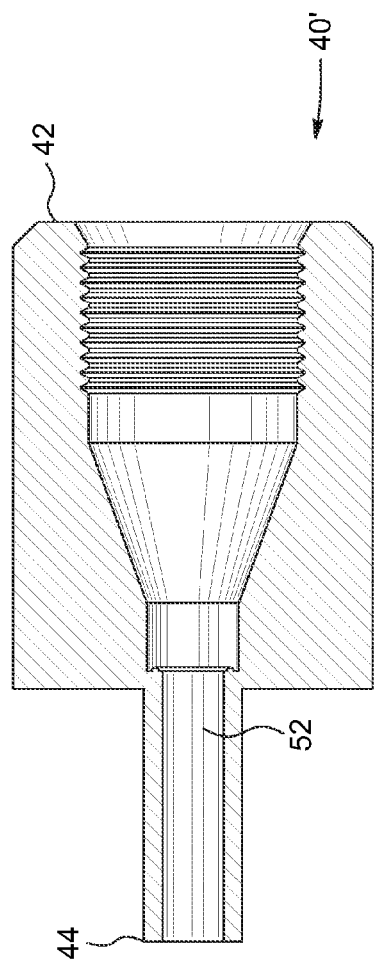

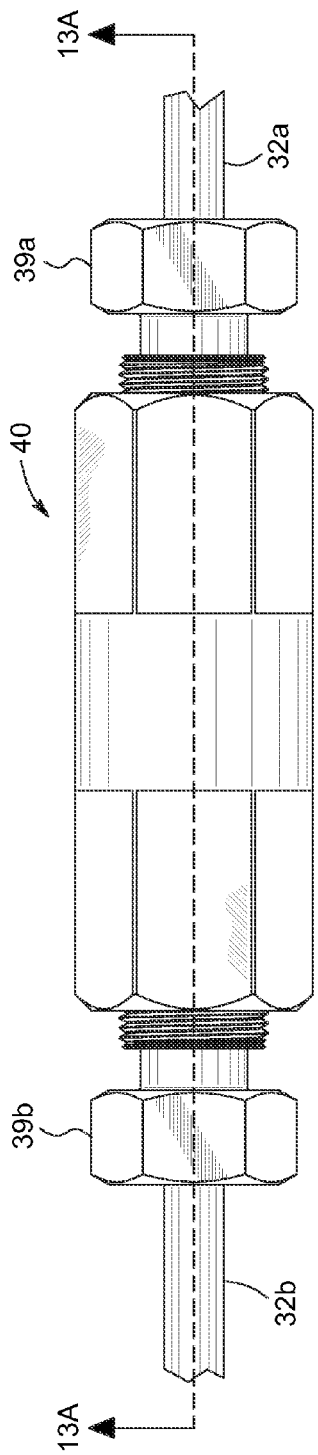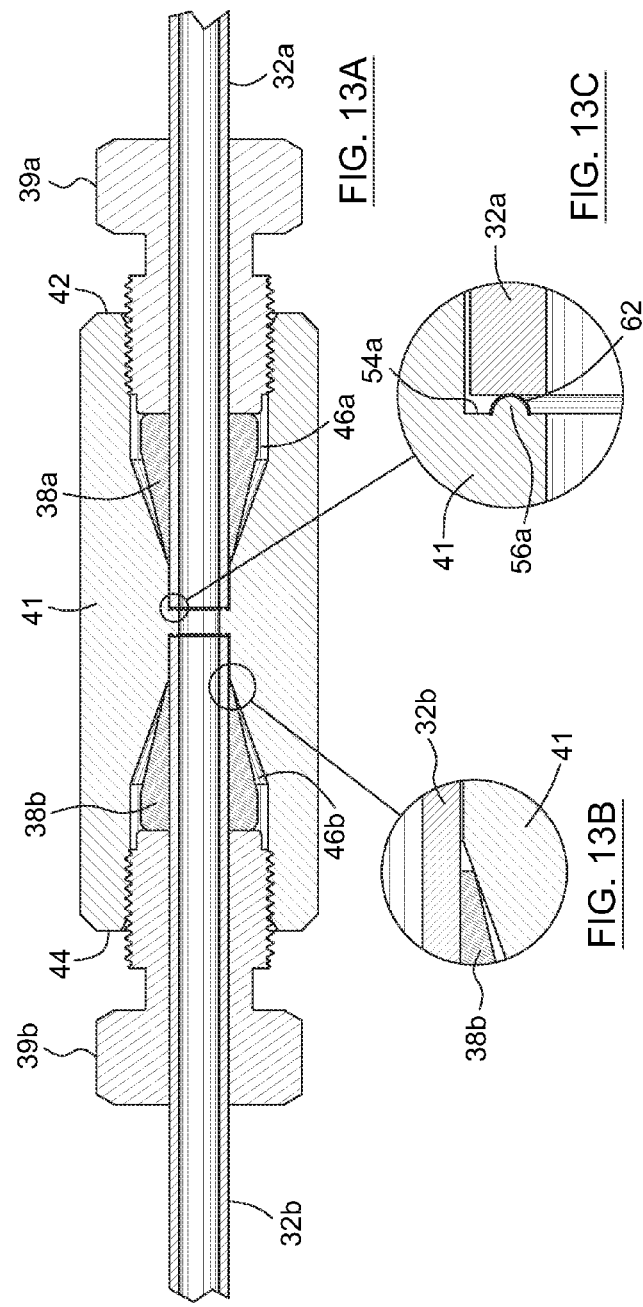

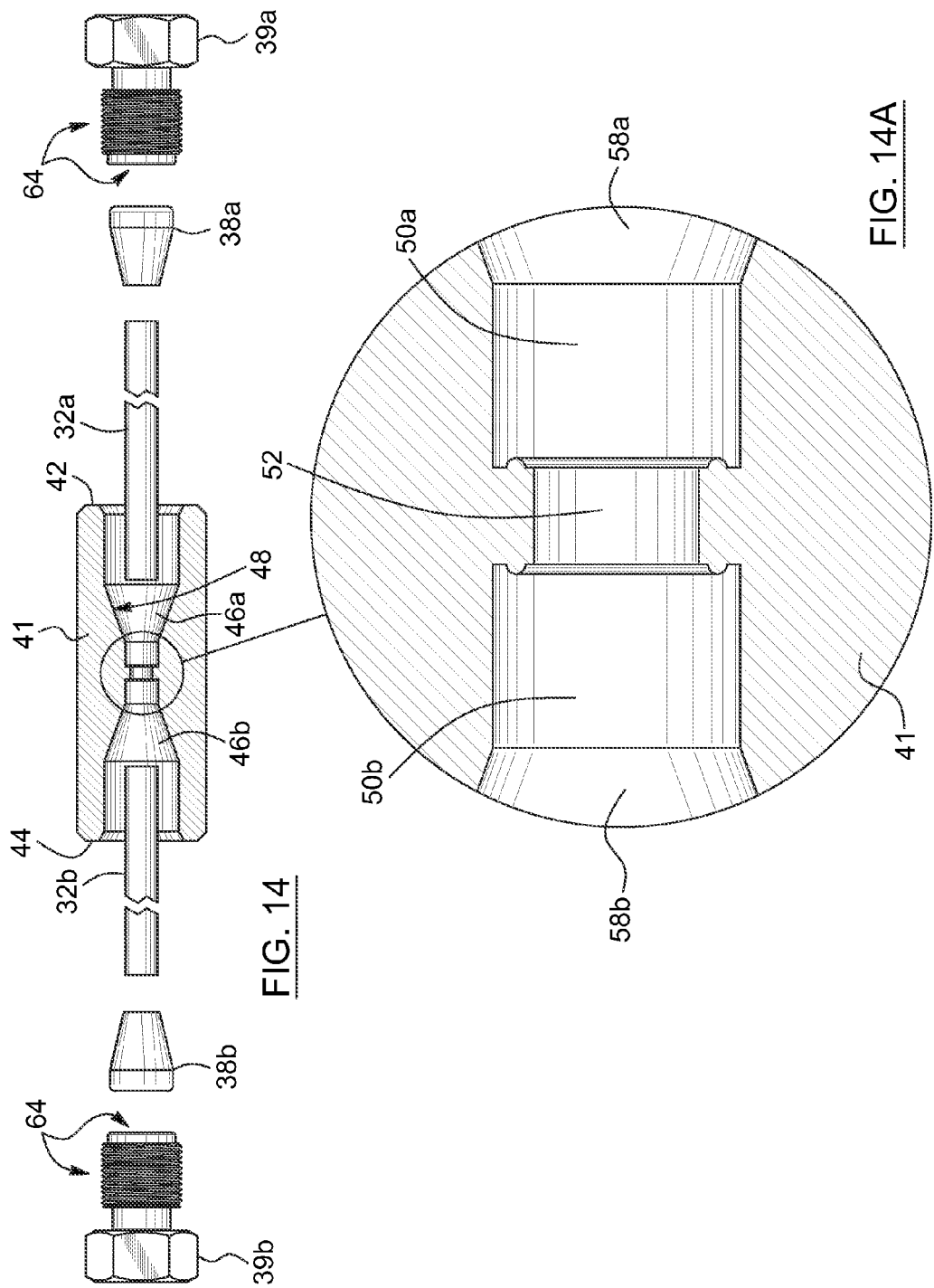

FITTING COMPONENT, FERRULE AND NUT

CROSS-REFERENCE TO RELATED APPLICATIONS

This application claims priority to U.S. Provisional Patent Application Ser. No. 61/450,184, filed Mar. 8, 2011, the entirety of which is hereby incorporated by reference.

FIELD OF THE INVENTION

The present invention generally relates to analytical devices, fitting component and unions, and more particularly concerns a compression fitting component adapted to receive and connect a tube, taken alone or in combination with a ferrule and a nut.

BACKGROUND

Fitting components and unions are commonly used to sealingly connect a tube to another device, to another tube, or simply to cap the tube. When used in analytical systems, fitting components and unions are most often used to sealingly connect two tubes together, in order to allow leak-tight fluid communication between the tubes. Fitting components can also be part of analytical devices and actuating mechanism for receiving different types of tubing.

One common type of fitting assembly 10 is shown in FIGS. 1 and 1A (PRIOR ART). A double ferrule 12, formed by a front ferrule 12a and a back ferrule 12b, pinches a tube 14 near its extremity, creating a bulge frontward of the ferrule 12, commonly known as a "swaging" of the tube 14. This swaging provides a good grip on the tube 14.

Double ferrule fitting assemblies are largely used in industrial applications such as in high pressure systems and/or in applications in which there is a high level of vibration. The bulging extremity of the tube 14 makes it very difficult to remove the tube 14 from the fitting 16 and thus creates a safe, seal-tight connection.

The widespread use of double ferrule fitting assemblies in industrial applications, along with their widespread availability, has led analytical system designers to use them in analytical instruments and sampling systems. The following paragraphs describe some of the drawbacks of fittings having a "swaging" action.

Scratches Generating Particles and Eventually Causing Leaks

Packed columns in gas chromatographic instruments must often be changed. A common reason for replacing the columns is the need for measuring new types of impurities in a new sample background. The outside diameter (OD) of these columns is typically of either 1/16" OD or 1/8" OD, and less frequently of 1/4" OD.

Referring to FIG. 1A, it is the "swaging" action of the tube 14 within the fitting 16 that creates the sealing and the tube gripping. The required torque to achieve proper sealing increases each time the tube 14 is inserted and retrieved from the fitting 16. When increasing the torque, the tubing 14 is forced deeper into the body of the fitting 16, although at some point the tube 14 cannot be moved forward, and its outside diameter cannot become larger, since the tube 14 is surrounded by the body of the fitting. With frequent assembly and disassembly of the tube 14 and the fitting 16, it becomes more and more difficult to pull out the tube 14 from the fitting 16, and even more difficult to re-insert the tube back in the fitting 16. This frequent assembly/disassembly of the tube 14 and the fitting 16 generates scratches inside the fitting 16 which in turn generates particles and eventually creates leaks at these locations.

In order to overcome these problems, one practice consists of cutting the tube just frontward of the front ferrule or of withdrawing the tube a little before tightening the nut 17, in order to eliminate the bulging of the tube[1]. While this practice reduces the difficulty to remove and reinsert the tubes within the fitting, it eliminates by the same occasion the safety properties, i.e. tolerance to very high pressure and vibration, of the swaging double ferrule type fitting. Even worse, this practice leads to another problem which consists in the creation of larger dead volumes.

[1]Agilent, 6890 User's Manual and, Site Preparation and Installation Manual

Dead Volume

In trying to resolve the problem caused by the "swaging" of double ferrule fittings, users have created a problem difficult to deal with, which are larger dead volumes. Indeed, by cutting/withdrawing the tubing', a larger volume between the extremity of the tube and the back, or seating portion, of the fitting is created since the space or volume previously occupied by the tubing is left empty.

With reference to FIG. 2, a simple gas chromatography (GC) system 18 is shown. In this case, the dead volume is present on both sides of the column since there is a fitting 10 on each end of the column. These dead volumes become problematic when there is a low carrier flow. Indeed, this will generate chromatographic peak broadening. Problems caused by scratches and generated particles are relatively easy to detect. However, problems caused by dead volumes are much more subtle, and can sometimes be mistakenly identified as leaks. In fact, dead volumes are often referred to as virtual leaks.

Still referring to FIG. 2, a sample gas 19 is injected on a separation column to separate the impurities and then to measure them by the integration of successive signal peaks by the detector 21, as well known in the art. The sample loop is swept by the sample gas 19, while the separation column and the detector 21 are swept by the carrier gas 23. In this example, the carrier 23 is helium, the column has an outer diameter (OD) of 1/8", a molecular sieve is used and the detector 21 is of the helium ionisation type. Such configuration is commonly used for permanent gas measurements. Each side of the column is provided with a double ferrule fitting 10, similar to the one illustrated in FIG. 1A. After starting up the system 18, helium is circulated and the column is regenerated to purge away any contaminants.

FIGS. 3 and 4 are graphics showing the level of impurities in parts per million (ppm) detected in function of the time in minutes. The graphic of FIG. 3 shows the signal of the detector of the system 18 from FIG. 2, after the system has stabilized, while the graphic of FIG. 4 shows the effect of varying the flow of the carrier on the detecting signal. In this case the variation consists of decreasing the flow of the carrier and then of restoring it. When carrier flow is decreased, the signal increases due to the presence of accumulated gas in the dead volumes, this accumulated gas diffusing back into the carrier. The presence of accumulated gas in the carrier increases the impurity level into the detector, thus increasing the detecting signal.

Restoring the flow of the carrier in the system dilutes the impurity level into the carrier gas, causing the signal to decrease. As it can be observed in the graphic of FIG. 4, the signal is lower after the restoration of the flow, in comparison to the signal at the beginning of the trend. This situation can be explained by the fact that there is less contaminant entrapped in the dead volume. Varying a system flow or pressure is a known method for finding leaks in gas chromatography system. However, when analyzing the signal trend of FIG. 4, one could think that there is leak and/or air diffusion in the system. A person skilled in the art would typically retighten the fittings until the signal decreases.

By retightening the fittings, the ferrules are pushed forward in the body of the fitting and the outer diameter of the tubing increases once again, thus decreasing the dead volume. By doing so, the entrapped contaminant is forced back into the carrier gas and detector.

Now referring to the graphic of FIG. 5, the signal shown illustrates the result of this action. Varying the flow or pressure to crosscheck for leaks would again generate a signal similar to the one illustrated in FIG. 4, but with less amplitude. Again, with the best intention in mind, an operator observing this would once again retighten the fittings, believing there are still leaks. The fact that there are also unions and other fittings at various locations in the system makes this problem even more difficult to track, identify and resolve. In the end, in attempting to resolve these virtual leaks, fittings will become over-tightened, and real leaks can be generated.

Single Ferrule Fitting Used in Analytical System

FIGS. 6, 6A and 6B show a single ferrule fitting assembly 20 commonly used in gas chromatography systems. The single ferrule 22 used in such an assembly 20 does not cause a "swaging" action, and the extremity of the tube 24 does not bulge out for holding the tube 24 in place in the body of the fitting 26. When the nut 28 is screwed in the fitting 26, the front edge of the ferrule 22 will grip the tube 24, creating a first sealing area. Another sealing point 33 is obtained between the external surface of the ferrule 22, and the internal surface of the fitting 26. The torque required to screw the nut 28 and push the ferrule 22 frontward in the fitting 26 is generally smaller than the torque required in the double ferrule design. In the double ferrule design, it requires extra torque in order to properly deform the tubing. With single ferrule fittings such as the fitting 26 shown in FIG. 6A, there is normally no deformation of the tube 24. In other words, the portion of the tube extending frontward of the ferrule 22 stays round and straight. The bottom or seating flange of the fitting 26 is where the square end of the tube seats within the fitting.

Best shown in FIG. 6B, the single ferrule fitting minimizes the formation of a dead volume precisely because the deformation of the tube 24 is reduced or eliminated. In order to prevent the tube 24 from being deformed, its diameter must be small enough so that the tube 24 can be slipped and fitted just tightly enough in the inner section of the fitting. Furthermore, the end of the tube 24 must be cut orthogonally, and have a clean and neat finish, in order to create a proper sealing surface with the corresponding squared bottom of the fitting.

Single ferrule fittings generally provide adequate results when the tubing size is smaller than ⅛" OD. As such, these fittings are sometimes referred to as "zero dead volume" fittings. However, a dead volume is still present in the fitting when in use, even if it is a small one. In particular applications, where high sensitivity systems are used, such as mass spectrometers and plasma emission detectors, the effect of small dead volumes can be observed.

Still referring to FIG. 6B, the dead volume 29a corresponds to the clearance between the outside diameter of the tube 24 and the internal surface of the aperture of the fitting 26. This dead volume 29a, no matter how small, will eventually be filled with fluid. It should be remembered that the diameter of the molecule of Helium is about 0.25 nm, Helium being a carrier commonly used in analytical systems. There is also a larger space or dead volume 29b located between the contact point 33 of the ferrule with the body of the fitting and the location where the tube enters into the pilot zone, ie where the tube 24 extends out of the ferrule 22. When temperature or pressure suddenly changes, these various volumes will eventually be filled with fluid.

In the single ferrule design, similar to the one shown in FIG. 6A, there is no real swaging action. However, in some cases, when tightening the nut to make a tube connection, the rotation force of the nut will be transmitted to the ferrule that also begins to rotate. The front portion of the ferrule will then rotate against the internal surface of the fitting body. This will eventually scratch the surface generating particles and leaks. Furthermore, there is a risk of twisting the front portion of the ferrule relatively to the rear portion. This will make it difficult to reseal the assembly during subsequent manipulations. Another common problem in single-ferrule industrial fittings such as the one illustrated in FIG. 6A is the loosening of the tubing 24 inside the fitting 26.

The Effect of Dead Volumes on Gas Chromatography Systems

Another erratic behaviour caused by dead volumes in chromatography systems can be observed when injecting a relatively large volume of a sample. Indeed, injecting a large volume of a sample suddenly reduces the pressure of the system, generating a "ghost" peak. This "ghost peak" is caused by trapped contaminants in the dead volume, diffusing back into the carrier. The larger is the tubing or the more sensitive is the system, the worse the problem will be.

As it can be seen from FIGS. 7 and 7A, a single ferrule fitting 26' is shown modified. This set-up allows monitoring the pressure variation in the internal volume of the assembly 20. A capillary hole has been pierced in the fitting 26' and an external capillary tube 25 is brazed in the body of the fitting 26'. On the other end of the capillary tube 25, a pressure transducer 27 is connected, and a pressure signal is monitored and trended by a data acquisition system 31. FIG. 7A shows more in detail the location where the pressure is measured, at the interface of the fitting 26' and the tube 24. The ferrule 22 is shown partially.

The graphic of FIG. 8 shows the pressure measured in the fitting assembly 20 of FIG. 7, in function of time. It can be seen that between times T0 and T1, the system is at atmospheric pressure P1. At T1, the system is pressurized at a pressure P2. Slowly the signal of the pressure transducer ramps up until P2 is reached. At T3, the pressure of the system is reduced to P1. Starting at T3, the signal of the transducer decreases until P1 is reached. Thus, between T3 and T4, the fluid entrapped in the dead volume is diffusing or depressurizing back in the main stream, this situation leading to a potential risk of contamination. It should be remembered that in some analytical applications, molecules are counted and that there can be a lot of them in this volume. Reducing this volume would certainly be beneficial.

Problems Related with Torque

It is known that smaller tubes require less torque to achieve a proper sealing. Tubes of 1/16" OD or 1/32" OD require less torque from the nut than those of ⅛" OD or ¼" OD. Most packed columns are made with ⅛" OD 304 stainless steel tubing, file cut. With this size of tubing, it is very hard to rotate the nut when it comes in contact with the ferrule. A higher rotating torque is required in order to move forward the nut so that the ferrule grips the tube. This operation is too difficult to perform while simply holding the fitting body in one's hand. Longer tools are required and very often tools such as vise grips are used to hold the fitting. Adding to the difficulty, these fittings must sometimes be replaced on columns located inside gas chromatography ovens or on critical and fragile components of analytical systems.

Another problem comes from the fact that the rotational torque applied on the nut is transferred to the ferrule, which then rotates or twists. Since the contact area between the nut and the ferrule is larger than the contact area between the tip of the ferrule and the body of the fitting, the rotational traction force is large and cannot be counterbalanced by the ferrule. Therefore, until the ferrule becomes really compressed on the tube and forced against the fitting body, it will rotate and/or twist. The rotation of the ferrule on the internal surface of the body of the fitting results in scratches on this surface, and eventually creates leaks. Such a problem is common for tubes having a size of ⅛" OD and even worse for tubes having a size of ¼" OD.

FIG. 9A shows how the nut 28 is turned in order to push the ferrule 22 towards the innermost portion of the fitting 26. FIG. 9B shows an undesired rotation of the ferrule 22, due to the transfer of the rotational movement of the nut 28 to the ferrule 22. The rotation of the nut 28 should result in a linear and frontward motion of the ferrule 22 in the fitting. For the reasons explained in the above paragraph, the rotational movement of the nut 28 often results in a rotational movement of the ferrule 22 against the inner surface of the fitting 26.

In light of the above, there is a need for improving the sealing a tube inserted in a fitting component, may it be a valve cap, a union or an actuating mechanism. There is also a need to further reduce dead volumes in fitting components. Yet still, there is a need for reducing or eliminating the rotation of the ferrule inside the fitting component. There is also a need to reduce the torque required to turn the nut in a compression fitting component.

SUMMARY OF THE INVENTION

An object of the present invention is to provide a fitting component addressing at least one of the above-mentioned needs.

The present invention provides a fitting component for receiving a tube. The tube has an inner diameter, an outer diameter and a tube end inserted through a ferrule. A portion of the tube end extends beyond the ferrule and is referred to as a pilot.

The fitting component comprises a body having first and second extremities. The body includes a cavity for receiving the tube end and the ferrule. The cavity is defined by an inner lateral wall and opens on the first extremity of the body. The cavity includes a pilot receiving section for receiving the pilot. The body also includes a channel connecting the cavity to another portion of the body. The channel has a cross-section smaller than a cross-section of the pilot receiving section. A radial annular flange is located at an interface of the pilot receiving section with the channel. The flange has an annular sealing lip protruding towards the cavity, the sealing lip being for forming a seal with a radial surface of the pilot.

By fitting component, it is meant any device which is part of an analytical system, or which is usable with an analytical device, and which is adapted to receive a tube and a ferrule.

Advantageously, the sealing lip provides a sealing ring or sealing zone between the extremity of the tube and this lip, when the tube is inserted and secured in the fitting component. The sealing lip also provides a good sealing of the tube within the fitting component, even if the cut end of the tube is not squared-cut, even if the tubes are not perfectly round or even if their external surface has been scratched.

Preferably, the annular sealing lip is coated with an inert substance softer than the fitting component. Still preferably, this inert substance is gold. Advantageously, the inert substance coating of the annular lip further improves sealing of the tube end with the radial flange of the fitting component.

Preferably, there is also provided the fitting component defined above in combination with a ferrule. The ferrule has a front portion with a tapered outer surface coated with an inert substance. Preferably, this inert substance is gold.

Advantageously, the inert substance coating the outer surface of the ferrule provides an improved sealing of the ferrule with the inner lateral wall of the fitting component, when in use.

Preferably, there is also provided the fitting component in combination with a threaded nut, the threads of the nut being provided with a lubricant. Alternatively, the threaded section of the fitting component can be provided with lubricant, instead of the nut. Preferably, the front surface of the nut devised to be in contact with the ferrule is also provided with lubricant. When the front portion of the nut is coated with lubricant, it is preferable that the back portion of the ferrule be left nude or uncoated. Alternatively, the front surface of the nut can be left uncoated, and in this case it is preferable that the back surface of the ferrule devised to be in contact with the nut be coated with a lubricant. Advantageously, a lubricant coating provided on the front surface of the nut or on the back surface of the ferrule, reduces or eliminates rotation of the ferrule against the internal surface of the fitting component when screwing the nut.

Preferably, the pitch between each of the threads of the nut is less than 1⁄32". This advantageously reduces the required torque when screwing the nut for compressing the ferrule within the fitting component. In other words, such a small pitch between each thread allows diminishing the required torque for sealing the extremity of a tube on the annular lip of the fitting component.

The other portion of the fitting component can be one of a cap for capping the tube end, a second tube for connection to another device; and a second cavity for receiving a device and for joining the tube to said device.

Alternatively, the other portion of the fitting component is a second cavity that comprises a pilot receiving section, a tapered ferrule receiving section, a threaded nut receiving section and a radial annular flange located provided with an annular sealing lip, similar to that of the first cavity. In this case, the fitting component is for joining the first and the second tube. The first and second cavities do not have to be identical: the fitting component can be used as a reducing fitting component for example.

There is also provided a fitting component kit for joining first and second tubes. The tubes have respective inner diameter and outer diameters and tube ends. The fitting component kit comprises:
  a fitting component;
  first and second ferrules;
  first and second threaded nuts.

The first and second ferrules and the first and second threaded nuts are for insertion around the tube ends of the first and second tubes, respectively.

The first and second ferrules are located frontward of the first and second threaded nuts, respectively. The portions of the respective tube ends extending beyond the ferrules are referred to as pilots. The fitting component comprises a body having first and second extremities. The body also comprises a bore extending from the first extremity to the second extremity. The bore includes first and second cavities respectively opening of the first and second extremities of the body and a channel connecting the first and the second cavities.

The first and second cavities are for respectively receiving the first and the second tubes. Each of the cavities comprises:

a pilot receiving section;
a tapered ferrule receiving section located next to the pilot receiving section; and
a threaded nut receiving section opening on a given one of the extremities;

The fitting component also includes a radial annular flange located at an interface of the pilot receiving section with the channel. The flange has an annular sealing lip protruding towards a corresponding one of the cavities, the sealing lip being for forming a seal with a radial surface of a corresponding one of the pilots. Each of the ferrules has an outer surface coated with an inert substance softer than the fitting component and each of said threaded nuts having a front surface and threads coated with a lubricant.

Other features and advantages of the present invention will be better understood upon reading of preferred embodiments thereof, with reference to the appended drawings.

BRIEF DESCRIPTION OF DRAWINGS

FIG. 7 is a partial cross-section view of the assembly of FIG. 6, modified for monitoring a variation of the pressure between the ferrule sealing point and the pilot receiving section. FIG. 7A is a close-up view of a portion of FIG. 7. (PRIOR ART)

FIG. 10 is a side view of a fitting component, according to a first preferred embodiment of the invention. FIG. 10A is a cross-section view taken along line 10A-10A of FIG. 10.

FIG. 11 is a side view of a fitting component, according to a second preferred embodiment of the invention. FIG. 11A is a cross-section view taken along line 11A-11A of FIG. 11.

FIG. 13 is a side view of the fitting component of FIG. 10, within its environment. FIG. 13A is a cross-section view of the fitting component of FIG. 13, taken along line 13A-13A. FIGS. 13B and 13C are two close-up views of portions of FIG. 13A.

FIG. 14 is an exploded view of the components shown in FIG. 13, in which the fitting component is shown in cross-section. FIG. 14A is a close-up view of a portion of the fitting component of FIG. 14.

DETAILED DESCRIPTION OF PREFERRED EMBODIMENTS OF THE INVENTION

Figure 1:
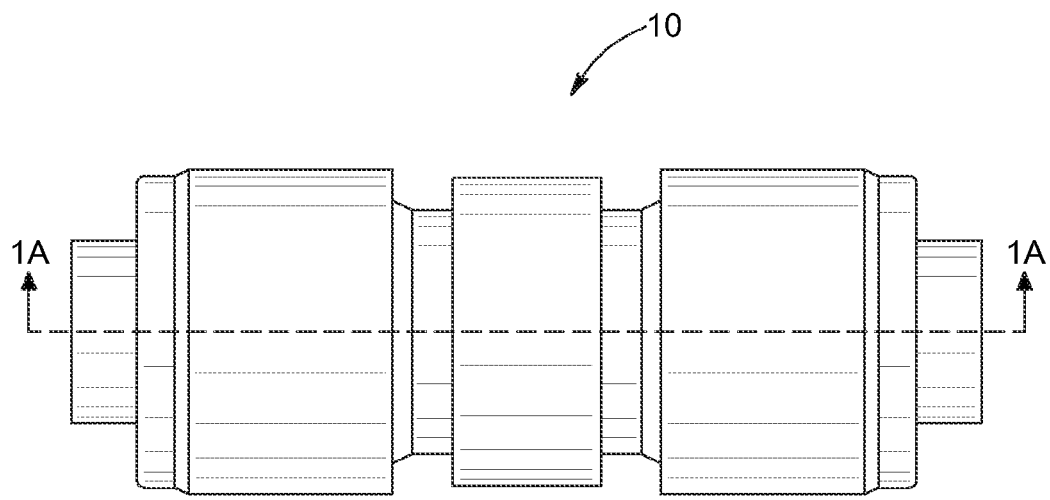
FIG. 1 is a side view of a prior art double ferrule fitting.
Figure 1A:
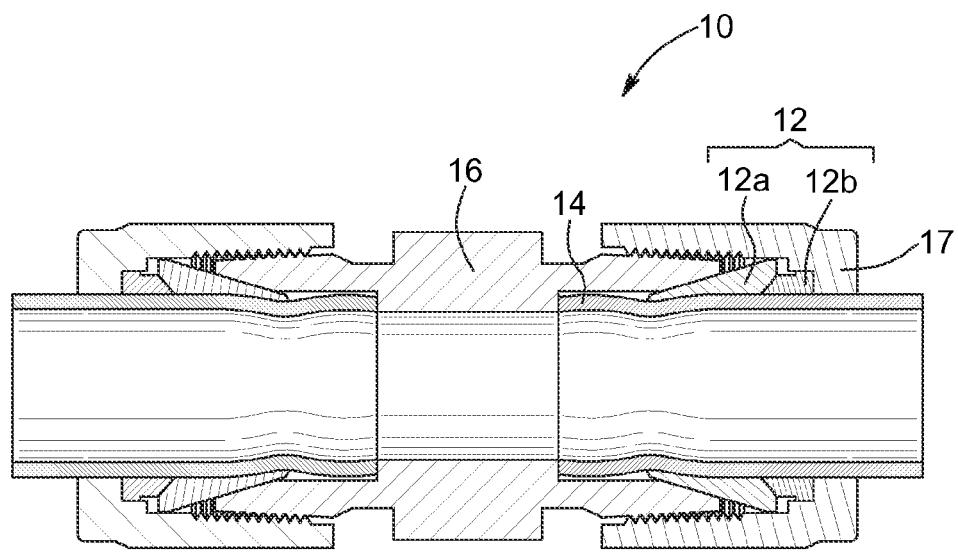
FIG. 1A is a cross-section view of the double ferrule fitting of FIG. 1, taken along line 1A-1A. (PRIOR ART)
Figure 2:
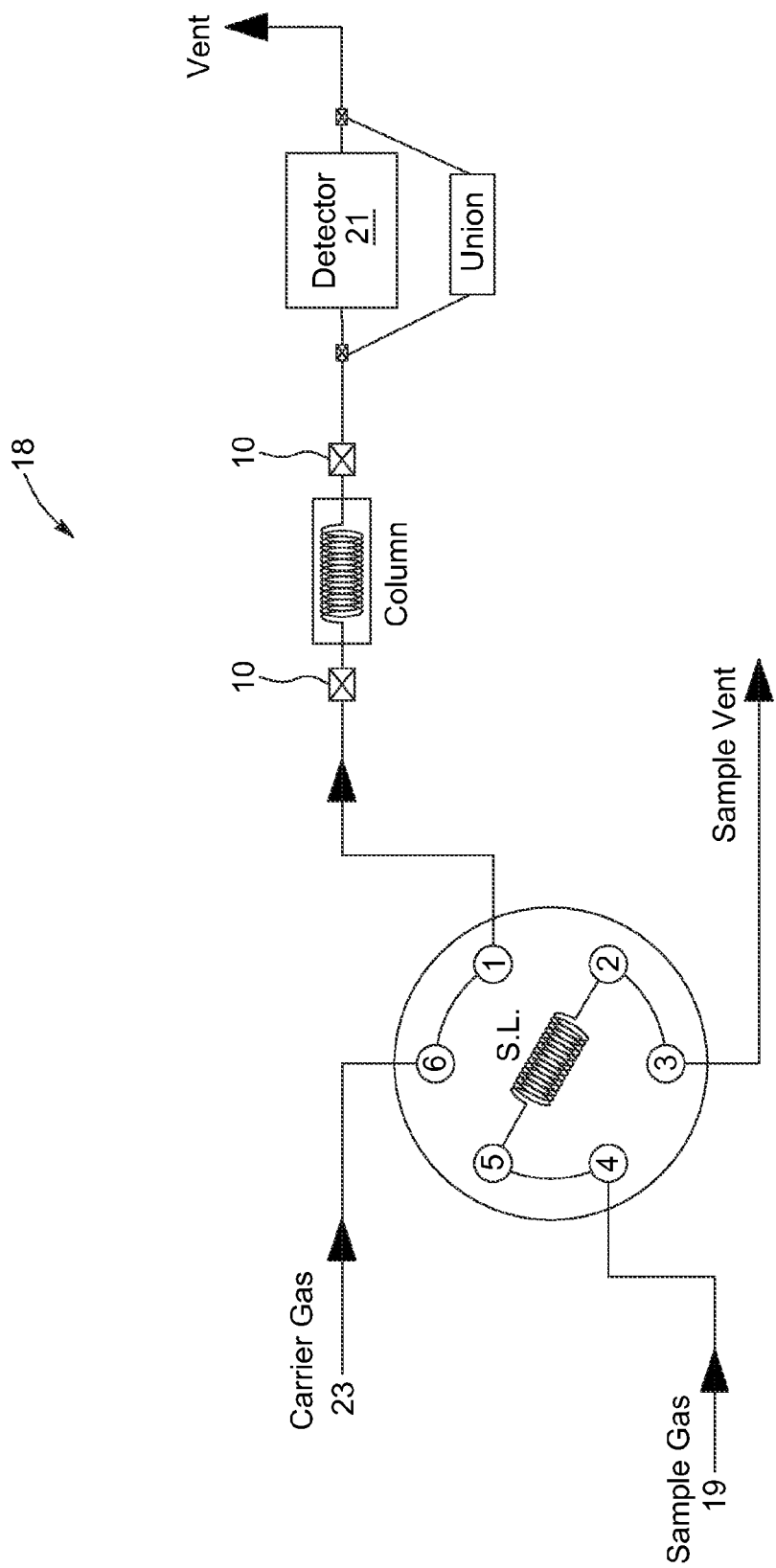
FIG. 2 is a schematic view showing a typical gas chromatography system. (PRIOR ART)
Figure 3:
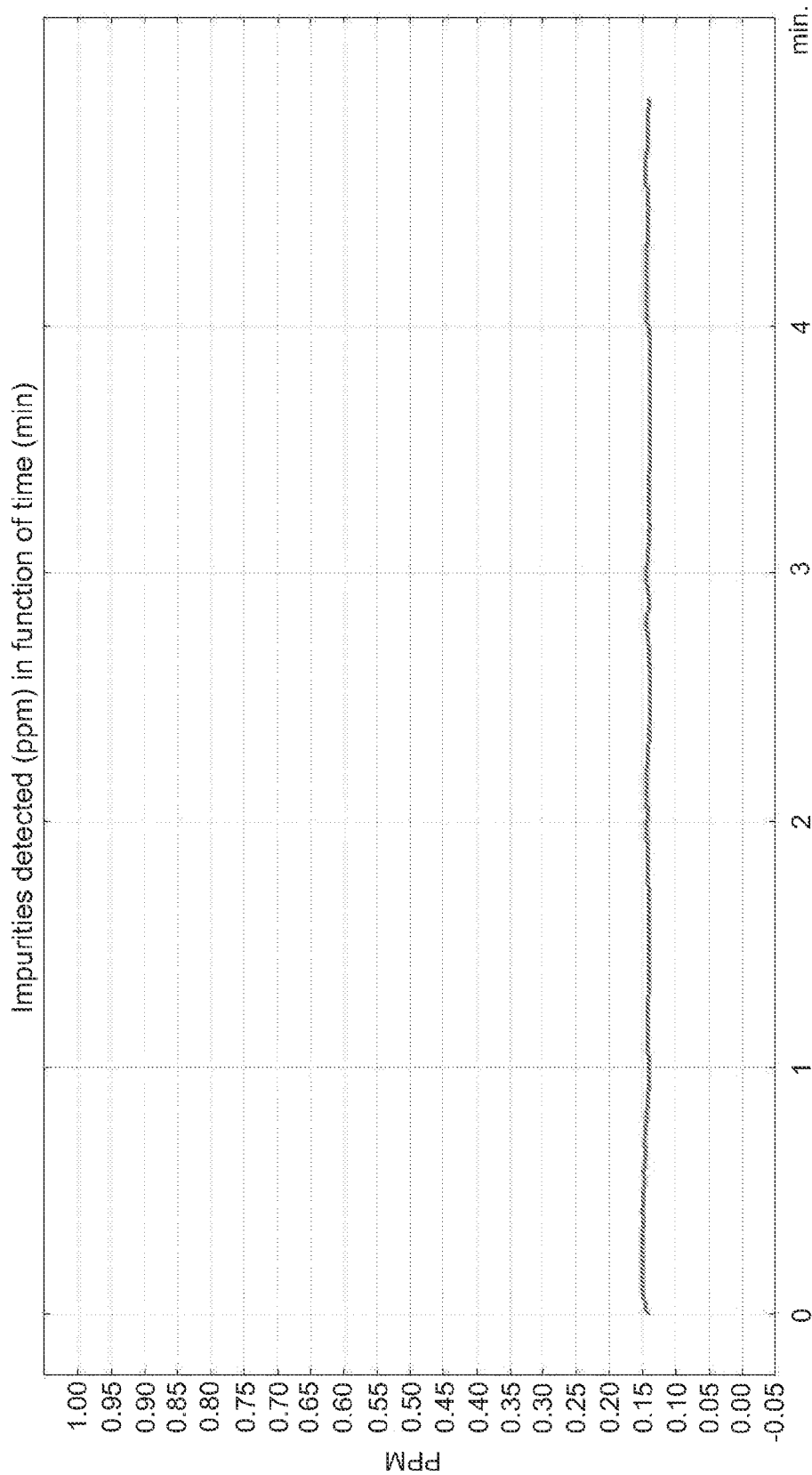
FIG. 3 is a graphic showing impurities detected (in ppm) in function of time, after system stabilization, using a prior art fitting. (PRIOR ART)
Figure 4:
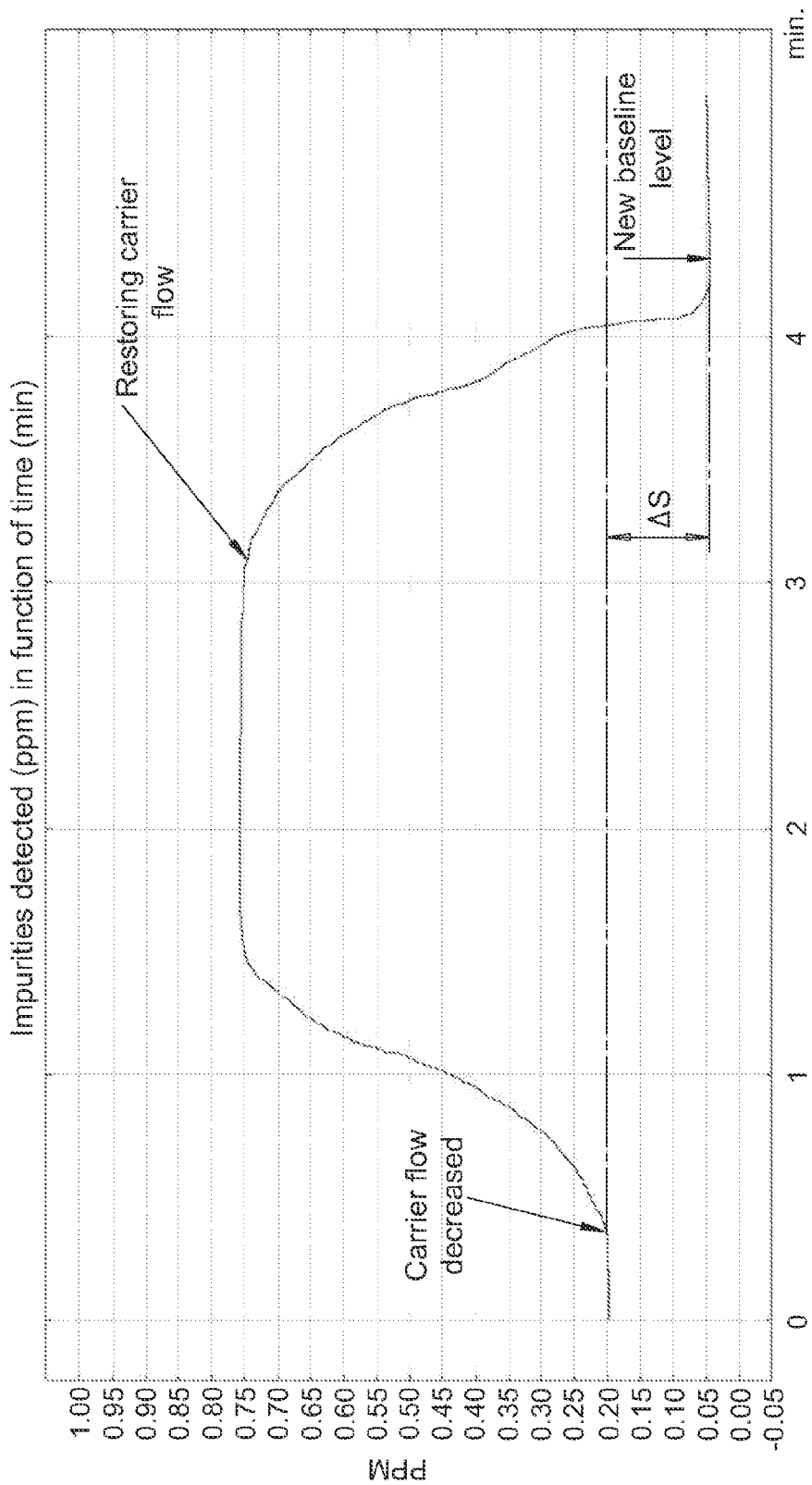
FIG. 4 is a graphic showing impurities detected (in ppm) in function of time, when the carrier flow is decreased and then restored, using a prior art fitting. (PRIOR ART)
Figure 5:
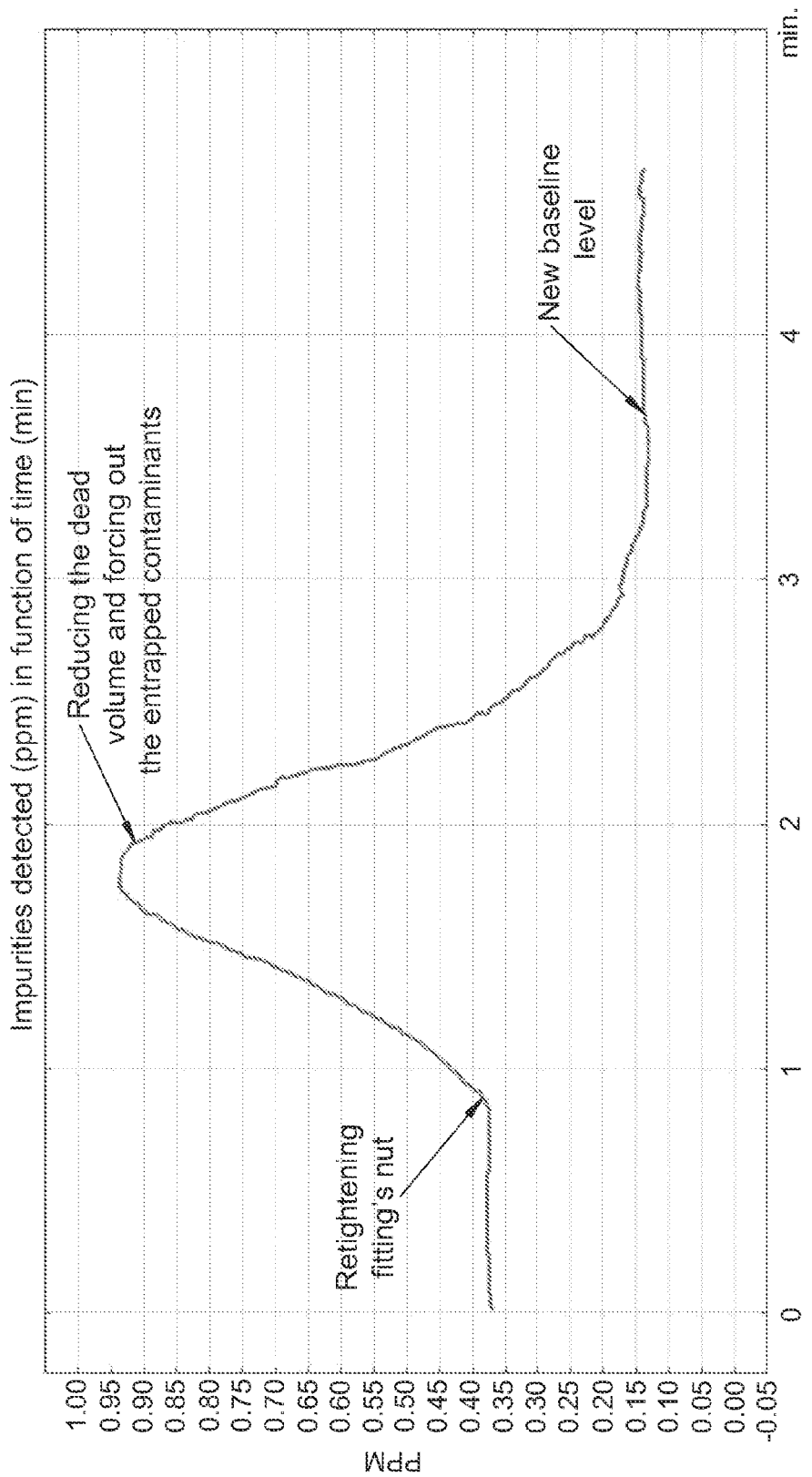
FIG. 5 is a graphic showing impurities detected (in ppm) in function of time, when retightening a prior art double ferrule fitting. (PRIOR ART)

In the following description, similar features in the drawings have been given similar reference numerals and in order to lighten the figures, some elements are not referred to in some figures if they were already identified in a preceding figure.

With reference to FIGS. 10, 10A, 11, 11A, 12 and 12A, fitting components 40, 40', 40" according to different embodiments of the invention are shown. By fitting component, is it meant to include any component part of an analytical system which is adapted to receive a tube inserted through a ferrule. A fitting component can be for example a fitting, a union, a cap, a valve, a valve cap, a valve body, a sealing plate, an instrument body or frame, an analyzer, sampler or separation module, a sample panel, a fluidic control component, an actuating mechanism and the likes. A fitting component is any analytical component or portion of an analytical component adapted to receive a tube locked in place with a compression nut and a ferrule. In other words, according to the invention, a fitting component can be integrally part of an analytical device; it can be a portion of such device, as well as a separate element, such as a "fitting" or "union", as a person skilled in the art would understand it. A fitting component allows connecting a tube to another device, such as a plug, another tube, an analytical module or system, and the likes.

Figure 10B:
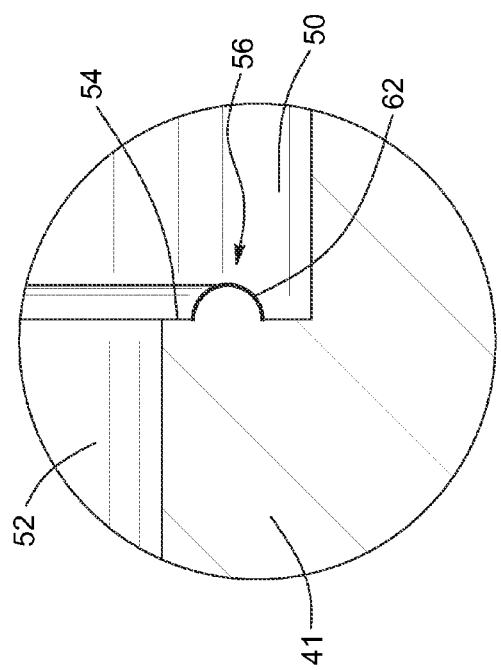
FIG. 10B is a close-up view of section 10B of FIG. 10A.
Figure 10C:
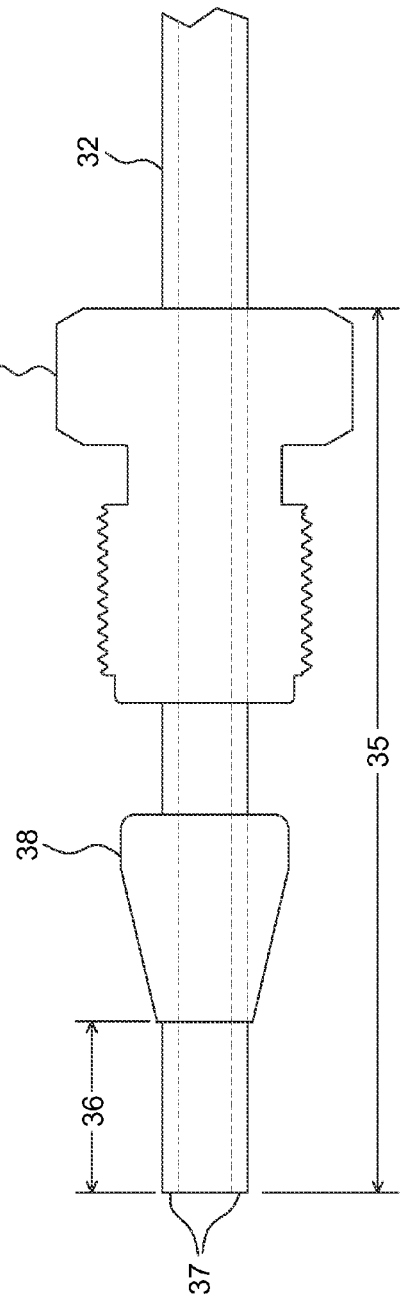
FIG. 10C is a schematic side view of a tube inserted through a ferrule and a nut, for insertion in a fitting component.

With reference to FIG. 10C, a tube 32, also called tubing, is shown. The tube 32 is for insertion in a fitting component of the invention. It has an inner diameter, an outer diameter and a tube end 35. The tube end 35 is inserted through a ferrule 38 and a nut 39. A portion 36 of the tube end 35 extends beyond the ferrule 38. That portion extending beyond the ferrule is referred to as a pilot 36. The pilot 36 as a radial surface 37.

Referring now to FIGS. 10, 10A and 10B, the fitting component 40 comprises a body 41 having first and second extremities 42, 44. The body 41 includes a cavity 46, best shown in FIG. 10A. The cavity 46 is for receiving a tube end, inserted through a ferrule and a nut. The cavity 46 is defined by an inner lateral wall 48, and opens on the first extremity 42 of the body 41. The cavity 46 includes a pilot receiving section 50 for receiving the pilot of the tube. The body 41 also includes a channel 52 which connects the cavity 46 to another portion of the body 41. In the present case, the other portion of the body is a second cavity similar to cavity 46. The channel 52 has a cross-section smaller than the cross-section of the pilot receiving section 50. The cavity 46 comprises a tapered ferrule receiving section 58, located next to the pilot receiving section 50, and a threaded nut receiving section 60 opening on the first extremity 42.

As best shown in FIG. 10B, a radial annular flange 54 is located at an interface of the pilot receiving section 50 with the channel 52. The flange 54 has an annular sealing lip 56 protruding towards the cavity 46. The sealing lip 56 is for forming a seal with the radial surface of a tube. Preferably, the sealing lip 56 is coated with an inert substance 62 softer than the fitting component. Preferably, this coating is gold.

With reference to FIGS. 11 and 11A, the fitting component 40' shown is provided with a tube extending from the fitting component. In this case, the fitting component 40' can be used as an adaptor, and the other portion of the body to which the channel 52 connects is a tube extending from the body of the fitting component 40', for connection to another device.

Figure 12:
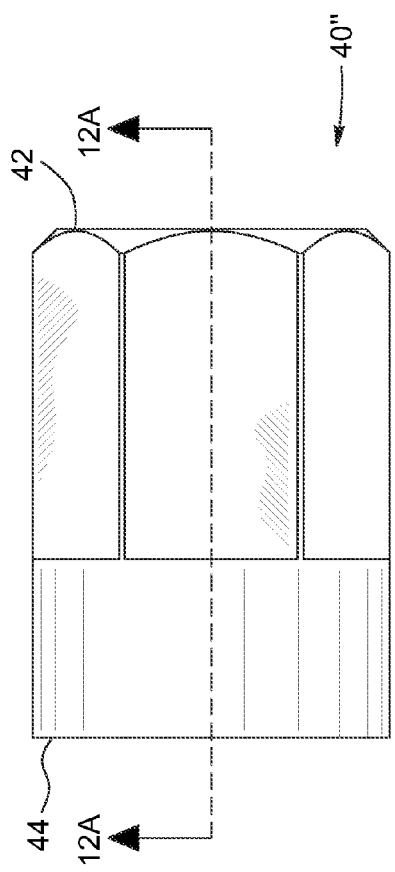
FIG. 12 is a side view of a fitting component, according to a third preferred embodiment of the invention.
Figure 12A:
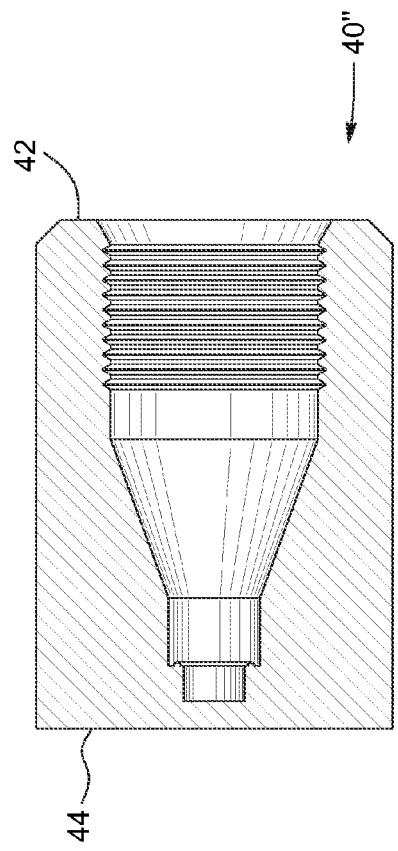
FIG. 12A is a cross-section view taken along line 12A-12A of FIG. 12.

With reference to FIGS. 12 and 12A, the fitting component 40" shown can be used as a cap, which is sometimes referred to as a plug. The other portion of the fitting component 40" is thus closed, for capping a tube end. In yet other embodiments of the fitting components, the other portion can be another cavity for receiving a device, allowing joining the tube to such device.

While the fitting components 40, 40' and 40" of FIGS. 10 to 12A are shown with an elongated body and two extremities 42, 44, other embodiments of the fitting component can be provided with different shapes, such as a T-shape or an X-shape, and a fitting component can include more than two extremities, and more than two cavities. Fitting components according to the present invention can also be provided with a threaded joint on one side and with a soldered joint on the other side.

Referring now to FIGS. 13 and 13A-13C, the fitting component 40 from FIG. 10 is shown in use, in combination first and second ferrules 38a, 38b and first and second nuts 39a, 39b, for joining first and second tubes 32a, 32b. The fitting component 40, the two ferrules 38a, 38b and the two nuts 39a, 39b together form a fitting component kit allowing joining the two tubes 32a, 32b. As shown, the first and second ferrules 38a, 38b, and the first and second threaded nuts 39a, 39b are for insertion around the tube ends of the first and second tubes 32a, 32b, respectively.

Figure 15:
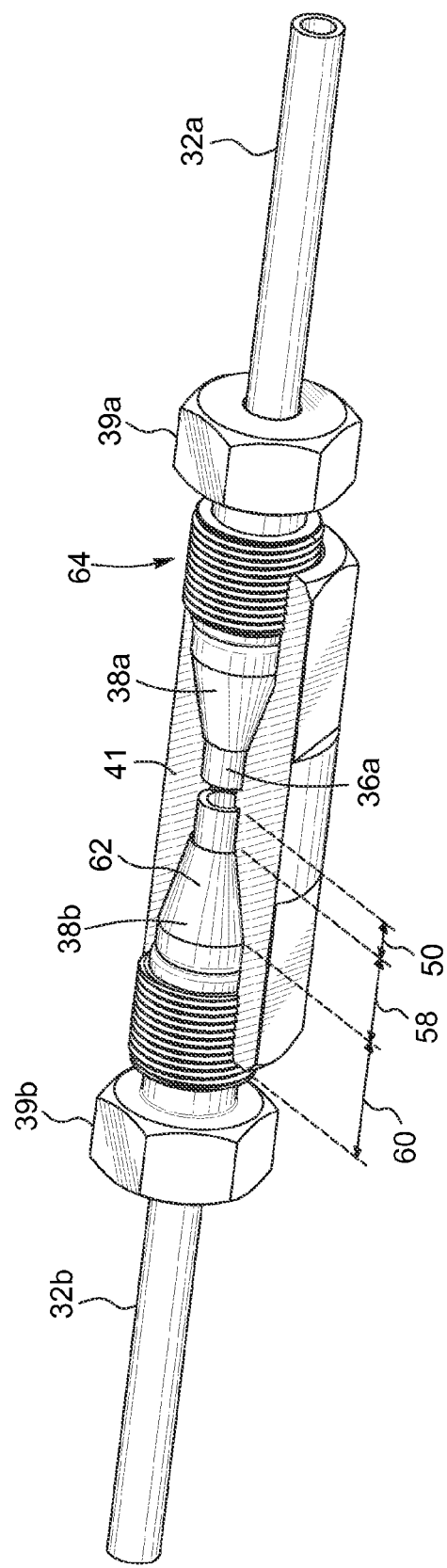
FIG. 15 is a perspective view of the fitting component and of the other components of FIG. 13, where only the fitting component is shown in cross-section.
Figure 16:
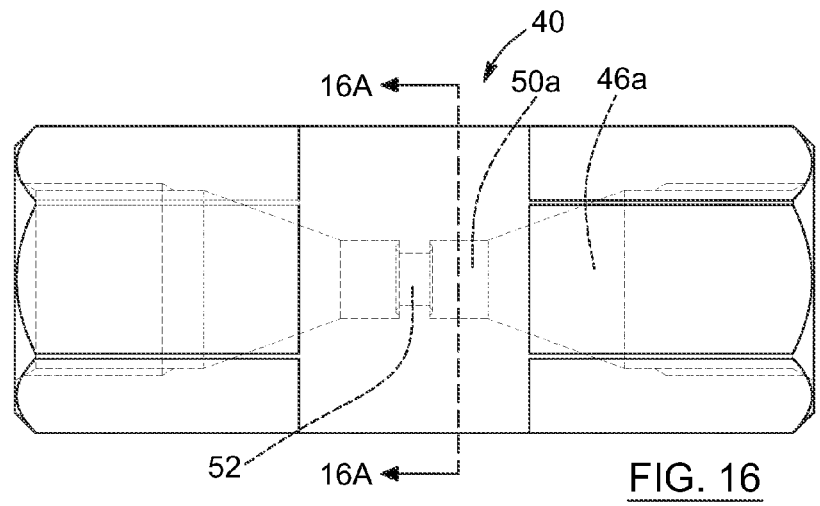
FIG. 16 is a lateral view of the fitting component of FIG. 13.
Figure 16A:
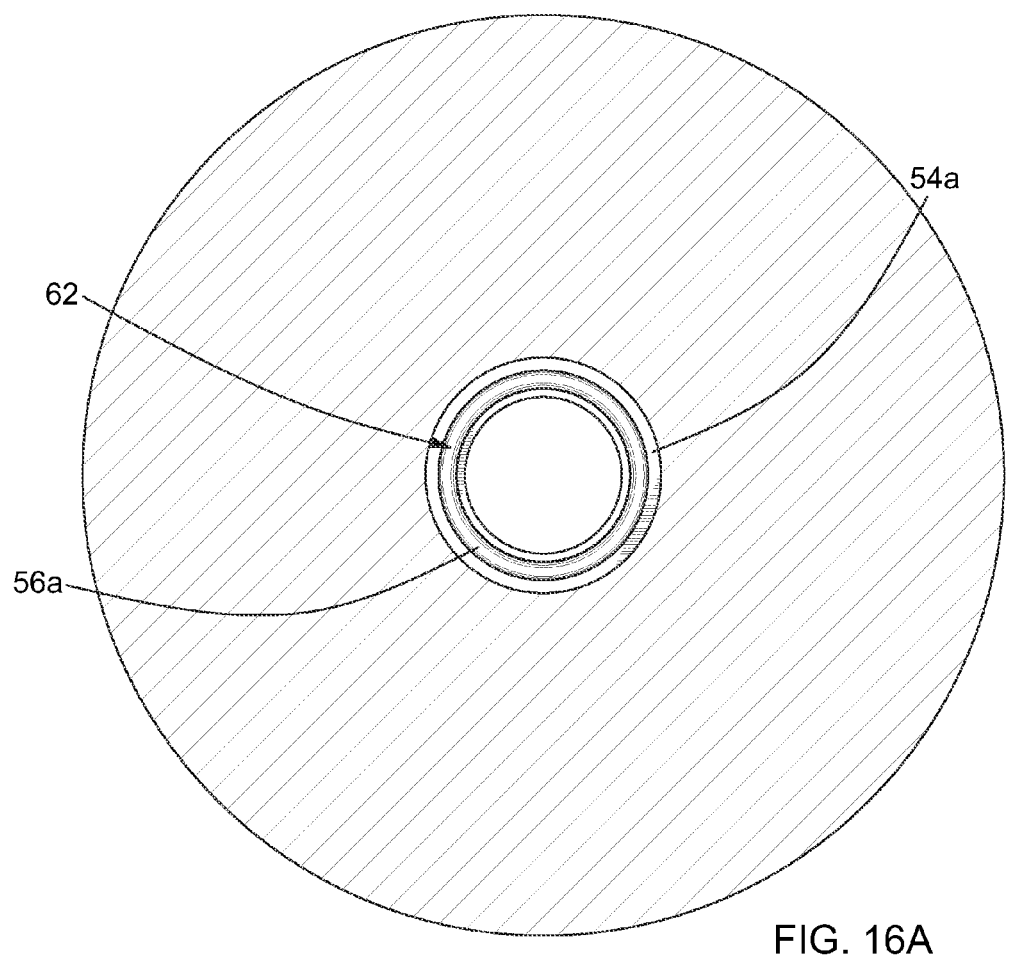
FIG. 16A is a closed up cross-section view of FIG. 16, taken along lines 16A-16A.

Referring to FIGS. 13A-13C, and also to FIGS. 14, 14A and 15, the fitting component 40 comprises a body 41 with first and second extremities 42, 44. A bore extends from the first extremity 42 to the second extremity 44. The bore includes first and second cavities 46a, 46b respectively opening of the first and second extremities 42, 44 of the body 41. A channel 52 connects the first and the second cavities 46a, 46b. The first and second cavities 46a, 46b are for respectively receiving the first and the second tubes 32a, 32b. It is preferable that the cross-section of the channel 52 corresponds to the inner diameter of the tubes 32a, 32b. While in FIG. 13A the cavities 46a and 46b are shown as being identical, the dimensions of the cavities do not necessarily need to be the same. For example, the fitting component can be a reducing fitting component for joining the first and the second tubes 32a, 32b, the second tube having an outer diameter smaller than the outer diameter of the first tube. In this case, the cross-section of the channel 52 would preferably correspond to the smaller inner diameter of the two tubes. For example, a fitting component of the invention can be used to join a first tube having an OD of 1/16" and an ID of 0.005" with a second tube having an OD of 1/32" and an ID of 0.010".

While in FIGS. 13 and 14, the fitting component shown consist of union, a fitting component according to the present invention can include a valve cap, a sealing plate or an actuating mechanism, or in fact, any analytical device having a flange provided with a sealing lip devised to be in contact with the pilot portion of a tube, such as shown in FIG. 13C.

Best shown in FIG. 15, each of the cavities comprises a pilot receiving section, a tapered ferrule receiving section located next to the pilot receiving section, and a threaded nut receiving section opening on a given one of the extremities. In FIG. 15, the pilot receiving section 50, the tapered receiving section 58 and the threaded nut receiving section 60 are indicated as such on the left side cavity only, not to burden the figure. On the right side of the fitting component, the pilot portion 36a of the tube 32a is shown extending frontward of the ferrule 38a, in the pilot receiving section.

With reference to 16 and 16A, a radial annular flange 54a is located at an interface of the pilot receiving section 50a with the channel 52. The flange 54a as an annular sealing lip 56a protruding towards the corresponding cavity 46a. In use, the sealing lips of each seating flanges are for forming a seal with the radial surface of a corresponding one of the pilots, as best shown in FIGS. 13C and 15.

Turning back to FIG. 15, in order to improve the sealing of the cut end of the tubes 32a, 32b with the corresponding sealing lips of the fitting component 40, the lips are preferably coated with a soft inert substance 62, such as gold for example. This substance is preferably softer than the material forming the tube, in order to improve the sealing of the tubes and the lips. The use of a soft inert coating on the annular lip is particularly advantageous for improving the sealing of tubes having been cut unevenly or presenting some imperfection at their extremity.

Still referring to FIG. 15, the ferrule 38b is for gripping the tube end of tube 32b, and for being compressed, or pushed, at least partially within the tapered ferrule receiving section 58. The ferrule 38b comprises a front and a rear portion. The front portion of the ferrule has a tapered outer surface while the back portion is devised to be in contact with the threaded nut 39b. Preferably, the front portion of the ferrule 38b is coated with an inert substance 62 softer than the fitting component. Alternatively, the entire lateral surface of the ferrule can be coated with an inert substance softer than the fitting component. Preferably, that substance is gold. Of course, ferrule 38a is also provided with the inert substance, such as for ferrule 38b. The gold layer improves the sealing; it is softer and easier to mate than the stainless steel surface of the fitting component body 41. With this layer of gold, there is less torque required to obtain proper sealing. Less torque further reduces the risk of a rotation of the ferrule 38a, 38b when screwing the nuts 39a, 39b for connecting the tubes 32a, 32b.

In use, when one of the nuts is screwed in the body of the fitting component, the corresponding ferrule first grips the tube. As the nut is screwed, the ferrule is compressed at least partially within the tapered receiving section. Then, as the ferrule is pushed forward, that is, towards the center of the fitting component, by the turning nut, the tube is compressed against the fine annular sealing lip. When proper tubing is used, an effective metal to metal seal is obtained. A tube material softer than the material forming the fitting component is preferred. For example, tubes made of annealed SS304 and a fitting component made of hardened SS316L have been conclusive. Having a fine lip, or sealing ring, distributes the mechanical force on a smaller area, thus increasing the effective seating force. The sealing lip penetrates the extremity of the tube. In fact, a first metal to metal seal section is created, with no dead volume.

Still referring to FIG. 15, but also to FIG. 13A, the extremity, or tip, of the front portion of the ferrules are advantageously elongated (or extended), compared to prior art ferrules, such as to extend far within the tapered section 58 of the fitting component. Preferably, the ferrule has a ferrule central axis and the front portion of the ferrule forms an angle with the ferrule central axis varying between 13 and 16 degrees. Best shown in FIG. 13A, by having the narrow end of the ferrules longer, more of the empty volume of the tapered ferrule receiving section is occupied by the ferrules, reducing the dead volume. It is also preferable that the front portion of the ferrules be provided with a sharp edge for gripping the tube. Yet still, if a longitudinal central axis goes through the fitting component, the tapered ferrule receiving section preferably forms an angle with that axis that varies between 18 and 20 degrees.

As best shown in FIG. 14, the front surface of the nuts 39a, 39b is coated or provided with a lubricant 64, for preventing a rotation of the ferrules 38a, 38b within the fitting component, when the ferrules are being pushed towards the center of the fitting component by the nuts. In this case, it is preferably that the rear portion of the ferrule devised to be in contact with the compression nut be left nude or uncoated. Of course, alternatively, the back surface of the ferrule can be provided with lubricant, the front surface of the threaded nut being left uncoated. It is best if only one of the two surfaces devised to be in contact be provided with a lubricant.

Preferably, the threads of the nut are also provided with a lubricant 64. Alternatively, the lubricant can be provided on the threads of the nut receiving section of the fitting component. Molybdenum disulfide is preferred for use as the lubricant, but other formulations can be considered.

By preventing a rotation of the ferrules against the inner wall 48 of the body 41, scratches within the fitting component are avoided, or at least reduced, in turn reducing a generation of particles and thus of contaminants in the analytical system where the fitting component assembly is used. In addition, by reducing the presence of scratches or marks on the inner wall 48 of the body 41, leaks are by the same occasion reduced. Scratches and marks create undesirable small channels or passages which can lead to pressure variation within the analytical system. Leaks also lead to contamination.

As explained earlier, the nuts 39a, 39b at each side of the fitting component are required to push the ferrules 38a, 38b farther onto the tubes 32a, 32b, such that the ferrules 38a, 38b eventually closes and sealingly surrounds the tubes 32a, 32b in the fitting component. Each nut 39a, 39b is provided with an inner through bore, and is devised to be slid over the tubes 32a, 32b. The head of a nut allows a user or operator to turn the nut so as to screw it within the threaded nut receiving section of the fitting component. The threads of the nuts 39a, 39b match the threads of the fitting component.

Advantageously, the pitch between each thread is less than 1/32", and preferably of 1/48", which is smaller than prior art nuts used in such fitting component assemblies. Reducing the pitch of the threads of the nuts provides the advantage of diminishing the torque required for screwing the nut in the fitting component, allowing a better control of the movement of the nut, and thus of the ferrule, within the fitting component. By changing the pitch and shape of the thread (for example by using a trapezoidal thread forms such as the Acme thread form) on the nut and inside the fitting component body allows for a smoother force transfer from the nut to the ferrule.

In addition, an anti-friction and anti-galling coating applied on the threads of the nut and on its front portion reduces the friction, for example by an order of 10 or more (10 representing the ratio of the coefficients of friction), reducing or eliminating the rotation of the ferrule when the nut is screwed. Another advantage of the reduced pitch and lubricant coating is that a fitting component assembly can be assembled with small tools, without requiring a vise. Furthermore, it reduces the risk of cold welding, and the nut is still easy to remove even when temperature has been cycled.

Figure 17:
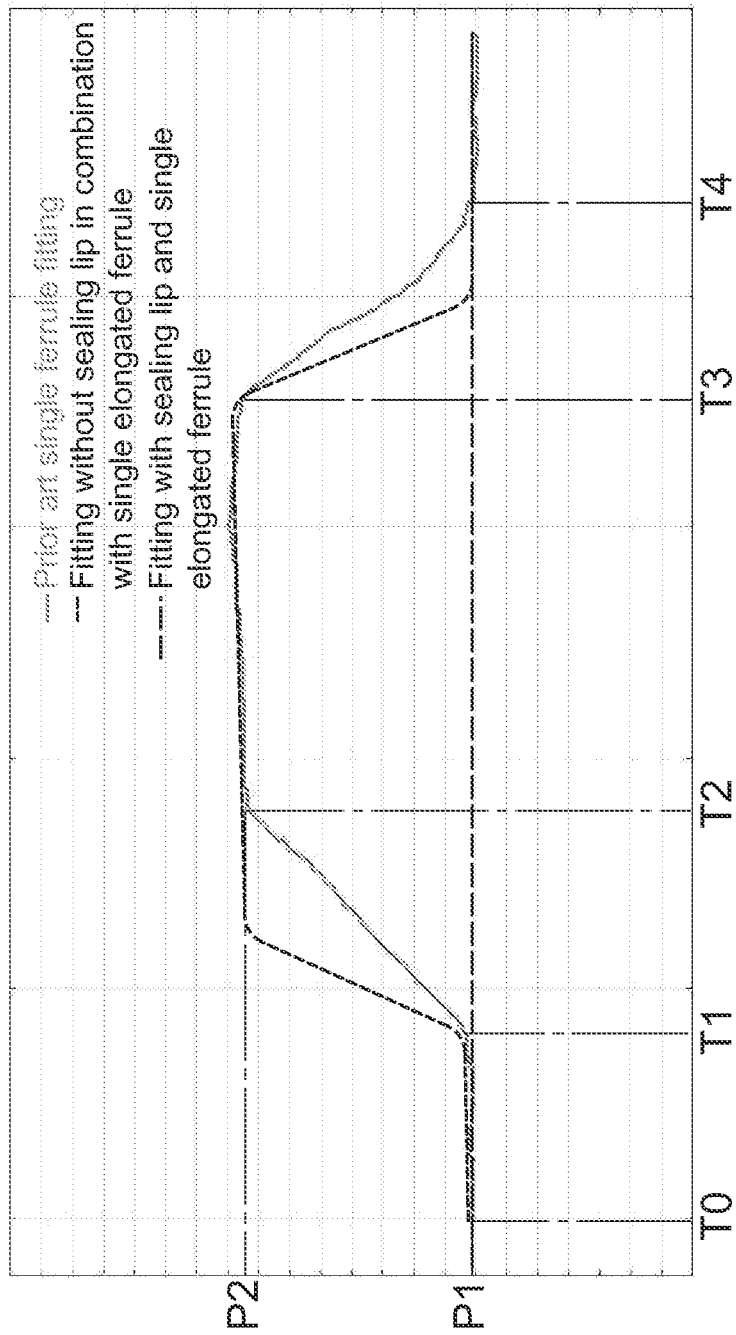
FIG. 17 is a graphic illustrating 1) the rise and fall of the pressure measured in the space surrounding the pilot in a prior art fitting component assembly 2) the rise and fall of the pressure measured in the space surrounding the pilot in a fitting component without sealing lip and used in combination with a single elongated ferrule and 3) the pressure measured in a fitting component provided with a sealing lip and a single elongated ferrule, in the space surrounding the pilot, according to an embodiment of the invention.

The graphic in FIG. 17 shows the pressure measured in the space surrounding the pilot when inserted in a fitting component. Experiments were conducted with a set-up similar to the one shown in FIG. 7, with three different types of ferrule assembly. In the first experiment, a fitting component assembly without a sealing lip used with a non-extended (or non-elongated) ferrule is tested. In the second experiment, a fitting component assembly without a sealing lip but used in combination with an elongated ferrule is tested. In the third experiment, a fitting component assembly with an annular sealing lip and with an elongated ferrule is tested. The rest of the components are the same in the three experiments, and the leak rate is assumed to be the same.

Still referring to FIG. 17, it can be seen that it takes more time to pressurize and depressurize the space surrounding the pilot when using the prior fitting component without a sealing lip and without an elongated ferrule. The higher rate of pressure rise/fall (while using a fitting component without any sealing lip but with a ferrule with an elongated tip) shows that the space is pressurized and depressurized faster. This indicates that a smaller dead volume is present when using a ferrule with an elongated (or extended) tip. In the last experiment, a fitting component with an annular lip is used. It can be see from the graphic that the pressure curve is steady at P1, indicating that the dead volume surrounding the pilot is negligible. Tubes having the same outside diameter were used in both experiments.

Figure 6:
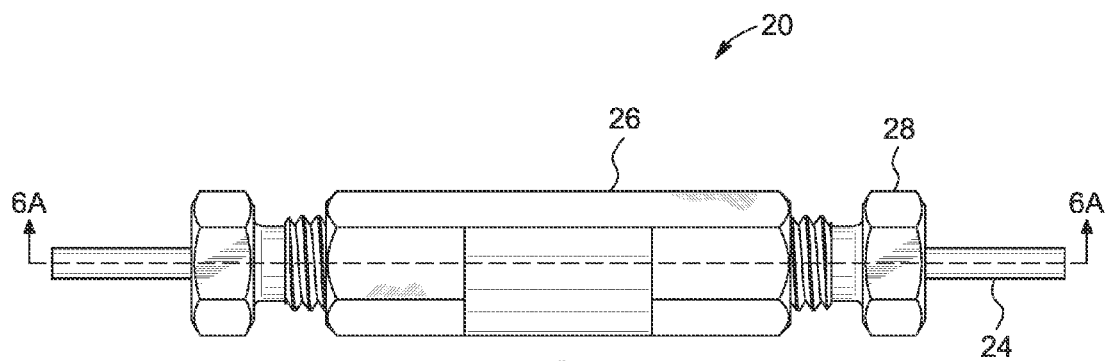
FIG. 6 is a side view of a prior art single ferrule fitting assembly.
Figure 6A:
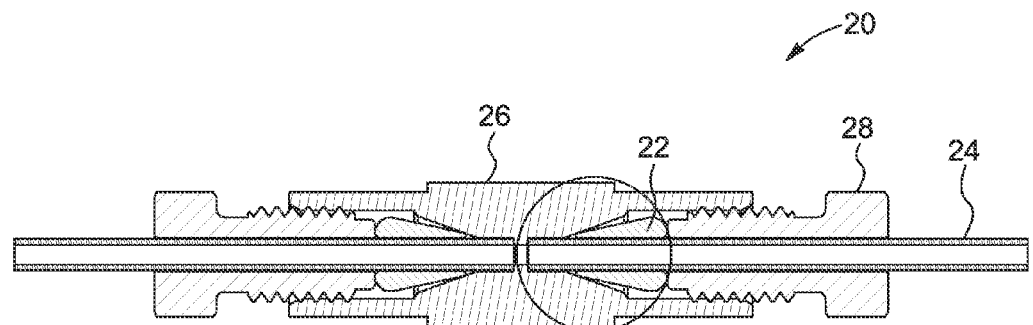
FIG. 6A is a cross-section view of the single ferrule fitting assembly of FIG. 6, taken along line 6A-6A.
Figure 6B:
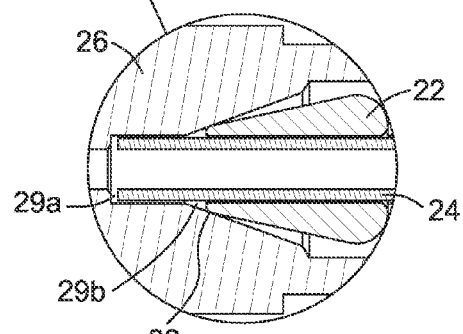
FIG. 6B is a close-up view of a portion of FIG. 6A. (PRIOR ART)
Figure 8:
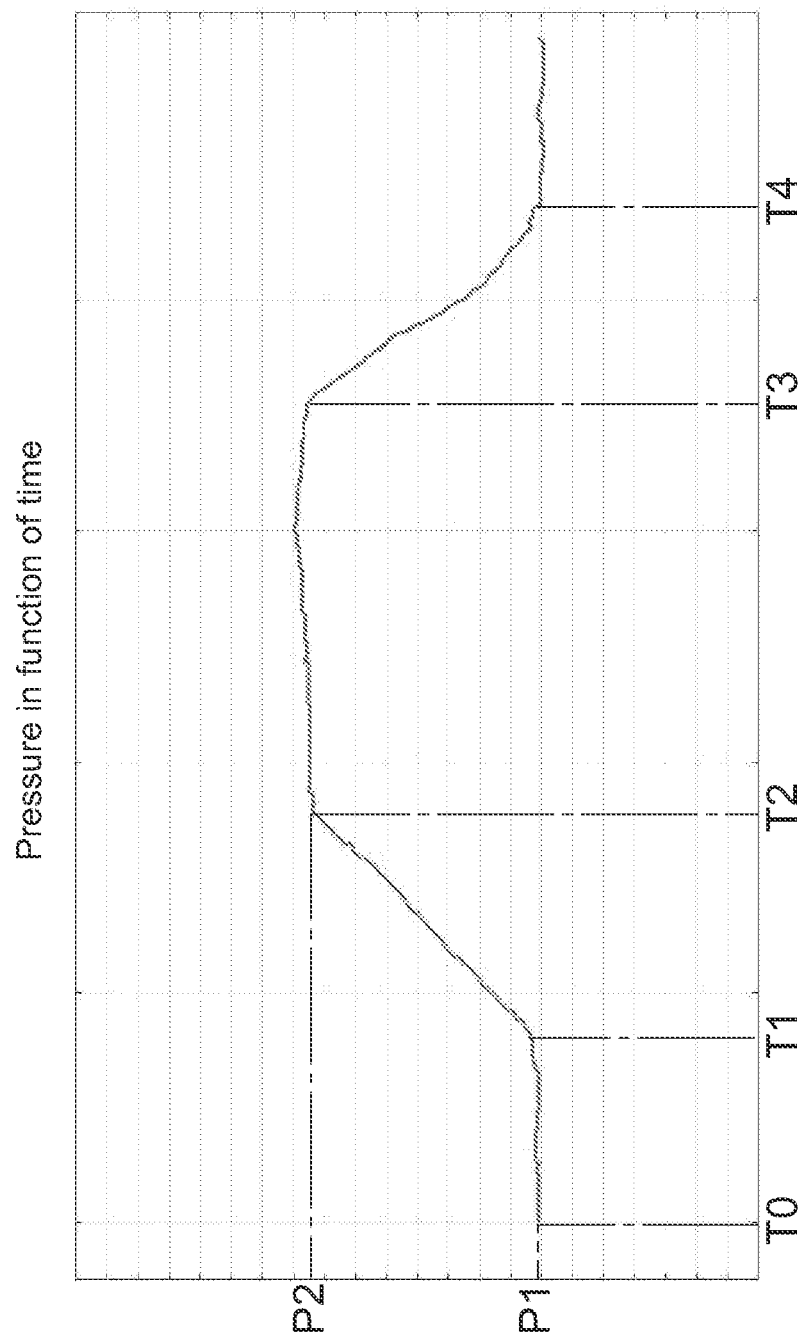
FIG. 8 is a graphic showing the pressure in function of time within a portion of the assembly of FIG. 7. (PRIOR ART)
Figure 9A:
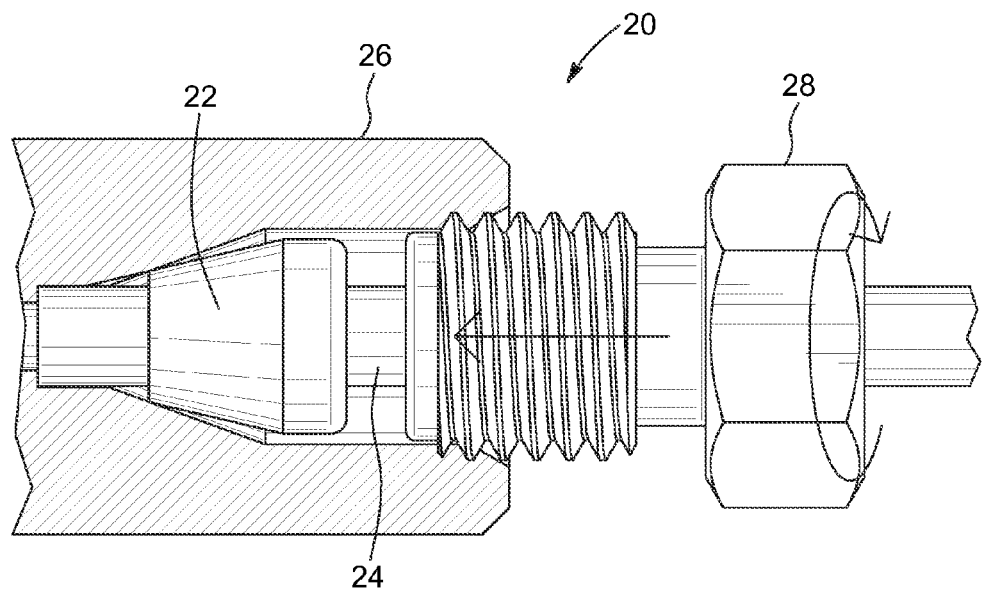
FIG. 9A is a partial view of FIG. 7, prior compressing the ferrule against the internal tapered surface of the fitting by the nut. (PRIOR ART)
Figure 9B:
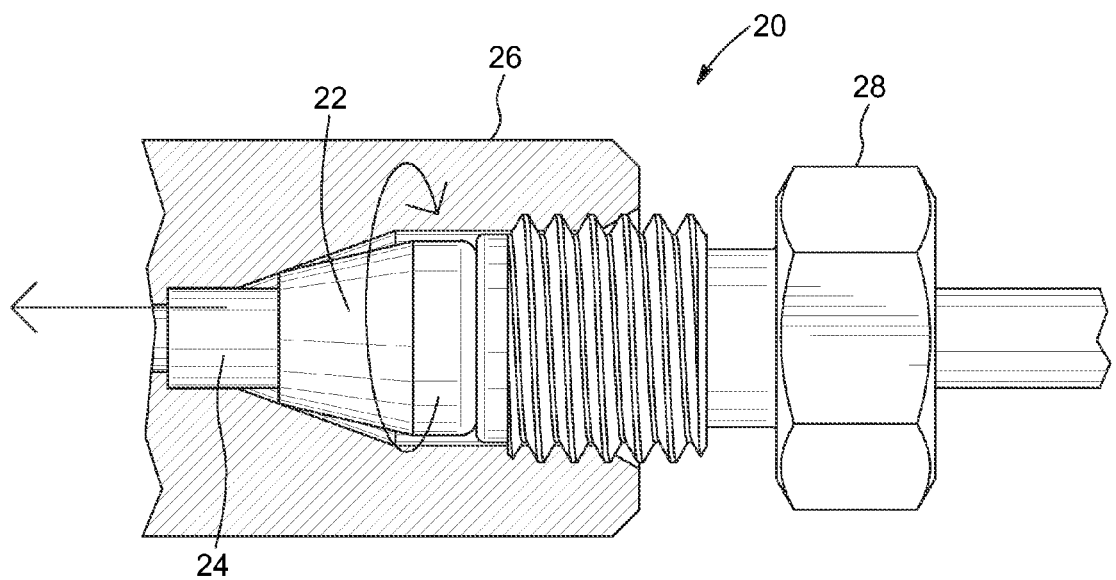
FIG. 9B is a partial view of FIG. 7, showing the nut pushing the ferrule against the internal tapered surface of the fitting. (PRIOR ART)
Figure 18:
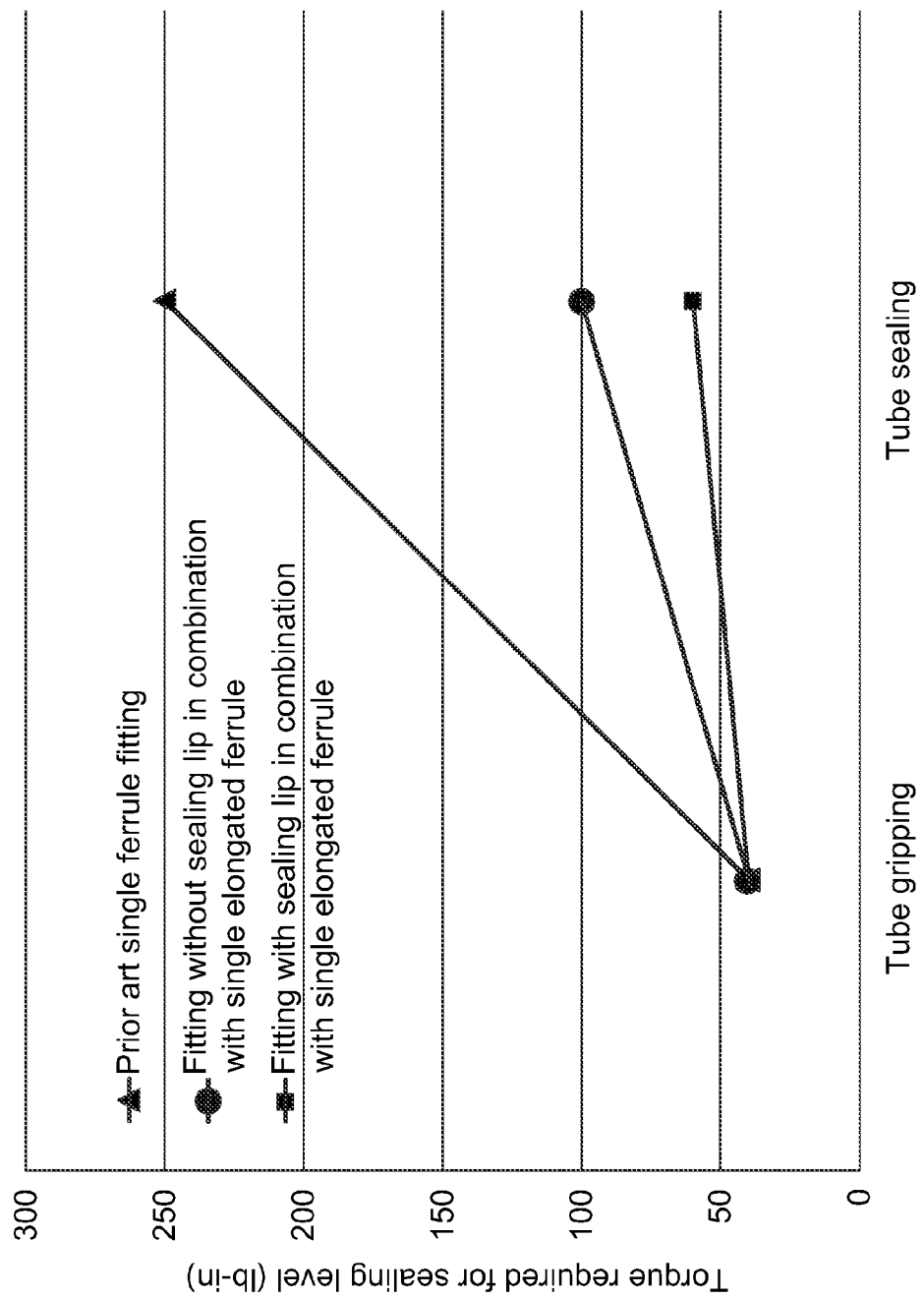
FIG. 18 is a graphic illustrating the required torque for achieving sealing 1) for a fitting component assembly of the prior art, 2) for a fitting component without sealing lip and with a single elongated ferrule and 3) for a fitting component assembly with a sealing lip and with a single elongated ferrule, according to a preferred embodiment of the invention.

Referring to FIG. 18, it can be seen that less torque is required when using a fitting component of the invention, in comparison to a prior art fitting component. The results for upper line were measured with a prior art single ferrule fitting component, such as the one of FIG. 6. The results for the lower line were measured with a fitting component such as the one shown in FIG. 13, the fitting component being provided with an annular sealing lip, in combination with a ferrule having an elongated tip. The graphic indicates that the required torque to achieve adequate sealing for a prior art fitting component assembly is much higher than for the fitting component assembly shown in FIG. 13 for example. For the lower line, the front portion of each nut was provided with lubricant. Lubricant was also used on the threads of the nuts.

Fitting Components Performance Comparison

Figure 19A:
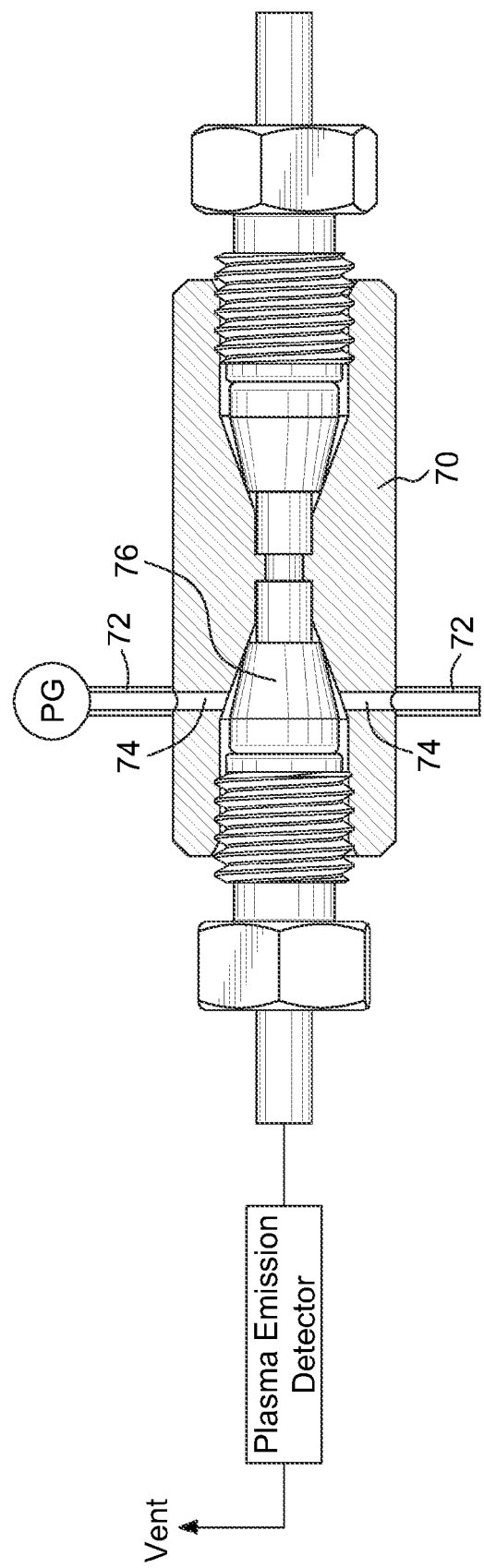
FIG. 19A is a cross-section view showing the set-up used to test the sealing properties of a prior art fitting component in function of the torque applied on the nut.
Figure 19B:
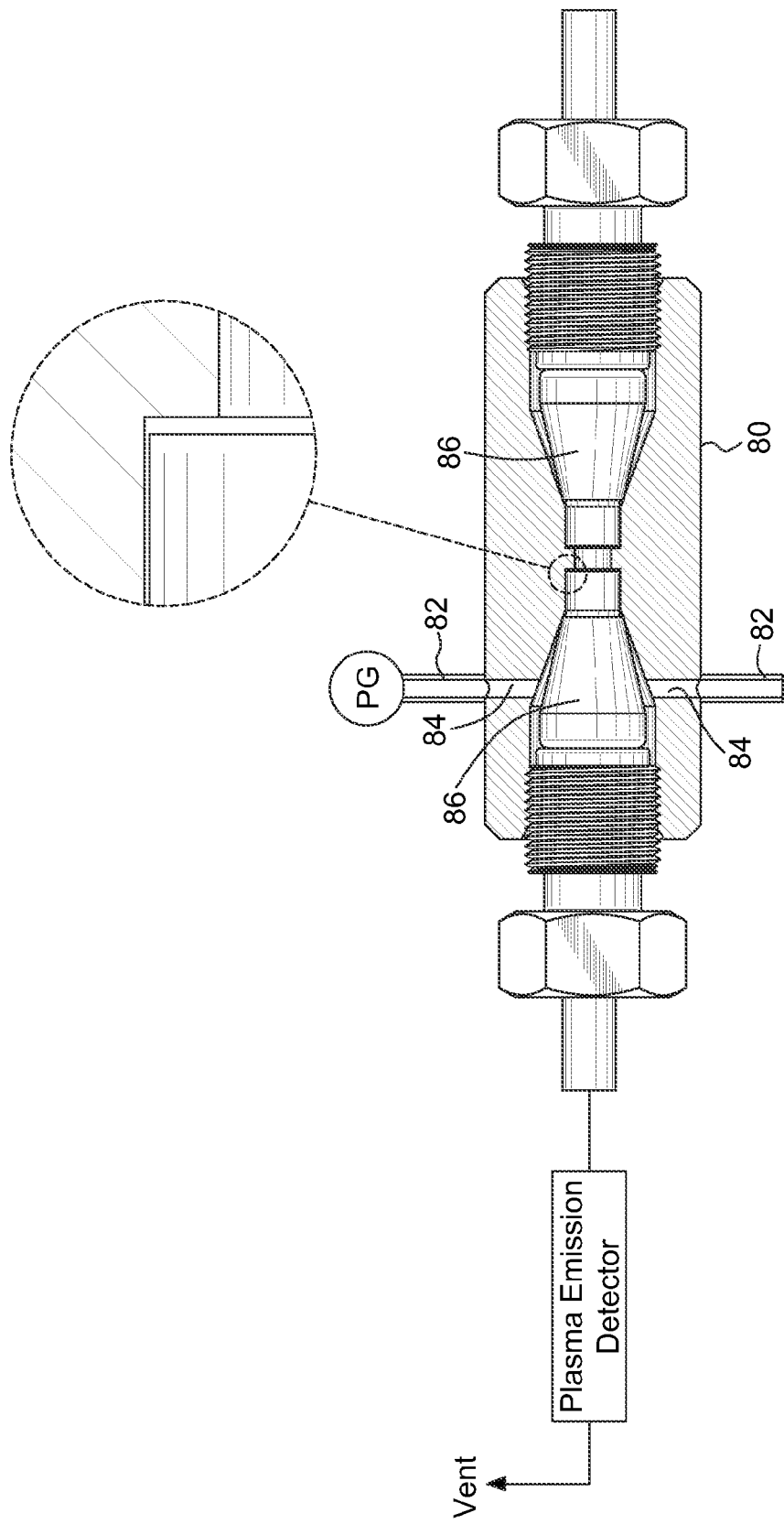
FIG. 19B is a cross-section view showing the set-up used to test the sealing properties of a fitting component without sealing lip and with a single elongated ferrule, in function of the torque applied on the nut.
Figure 19C:
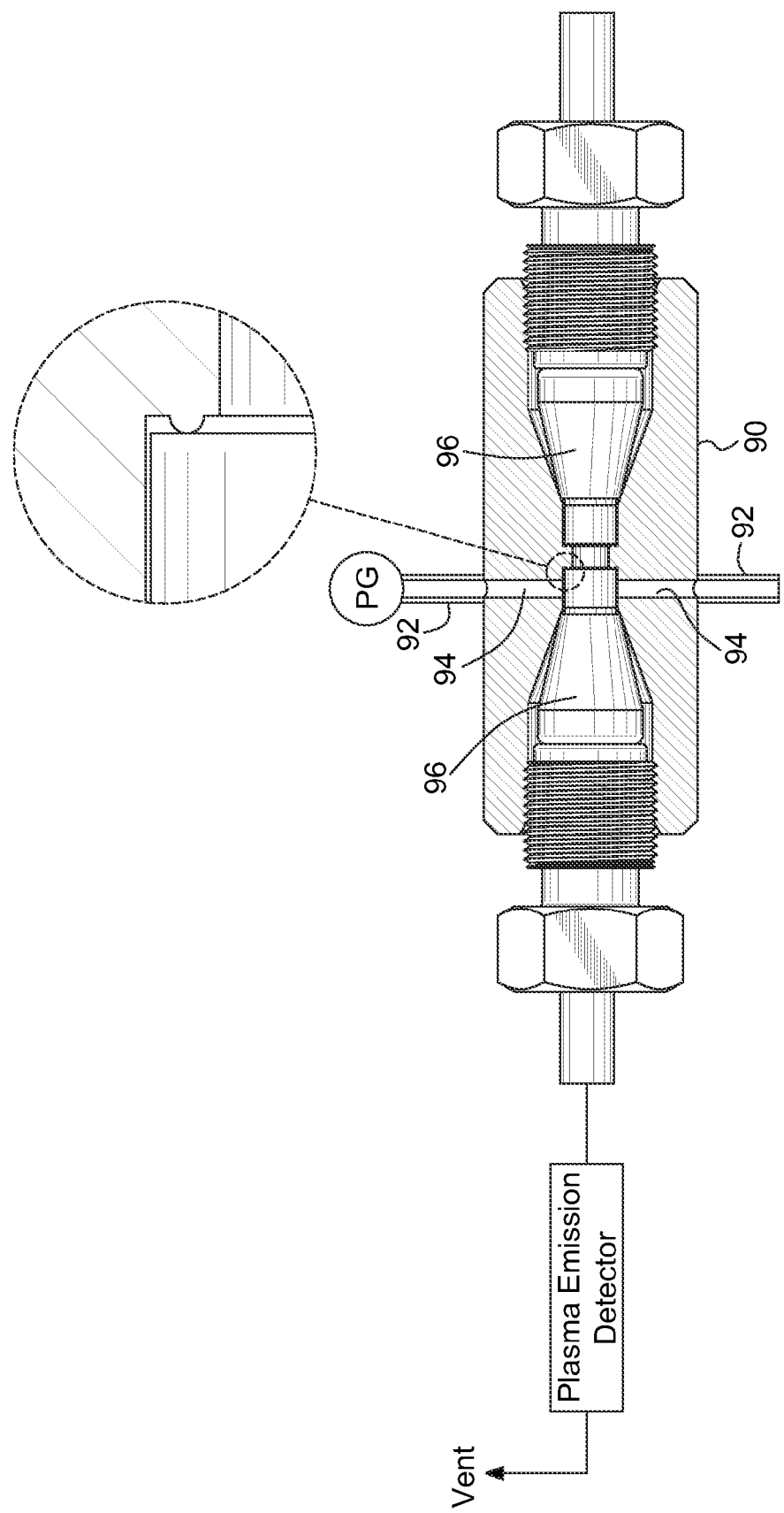
FIG. 19C is a cross-section view showing the set-up used to test the sealing properties of a fitting component with a sealing lip and with a single elongated ferrule according to a preferred embodiment of the invention, in function of the torque applied on the nut.

With reference to FIGS. 19A-19C, comparison tests were conducted to evaluate the sealing performance of the following fitting components: a fitting component 70 and a ferrule 76 of the prior art (FIG. 19A); a fitting component 80 without a sealing lip and with a ferrule 86 having an elongated tip (FIG. 19B), and a fitting component 90 with a sealing lip, in combination with a ferrule 96 having an elongated tip (FIG. 19C). These tests were conducted in order to further validate the advantages of by the present invention.

To do so, modified fitting components were used, such as the ones shown in FIGS. 19A-19C. In FIGS. 19A and 19B, the fitting components 70, 80 have been modified to allow pressurization of the internal volume between the threaded section and contact point between the ferrule and the body of the fitting component. In FIG. 19C, the fitting component 90 is modified to measure the pressure in the area surrounding the pilot.

With reference to FIG. 19A, fine channels 74, 84 have been pierced and external 1/16"OD tubes 72, 82 were inserted in the channels 74, 84 and brazed on the both sides of fitting components 70, 80. One of the tubes 72, 82 is used to send in pure nitrogen in the tested area, while on the other tube, a pressure gage PG was installed.

Now referring to FIG. 19C, the modified fitting component 90 used included a sealing lip. Channels 94 were pierced between the sealing lip and the sealing area between the ferrule 96 and the fitting component 90, as this is the area to be tested for this fitting component.

The following test was conducted with the test bench as illustrated in FIGS. 19A-19C. For each test bench, purified argon is flown at atmospheric pressure through axial tube of the fitting component, while the brazed tube (72, 82 or 92) of the fitting component is pressurized with pure $N_2$. The fitting component (70, 80 or 90) is connected to a Plasma Emission Detector tuned to measure the intensity of the $N_2$ emission line at 337.1 nm. Other types of $N_2$ sensitive detectors could also be used. Such systems have found leaks that were undetectable with Helium based mass spectrometer leak detector. This set up is also very sensitive to measure inboard leakage. Indeed the fitting component (70, 80 or 90) is surrounded or "immersed" in a "sea" of air, which has about 79% $N_2$. Compared to the 5 ppm of Helium normally found in atmospheric air, which the Helium mass spectrometer based leak detector relies on to find such a leak. The $N_2$ as a tracer is more sensitive and the system is much less complex. This set up is used by AFP™ for the leak rate certification. The gas is passed through a 0.5 micron particle filter before being introduced to the fitting component under test. This is to make sure that fitting component performance test will not be affected by particles being introduced into a fitting component. This system has 4 to 5 times the sensitivity for leak detection than a standard Helium mass spectrometer leak detector[2].

[2]Varian Mass Spectrometer Manual, Part Number 0981-6999-09-070, September 1995, P.P. 3-10, 3-11

Once the test bench is properly set-up, the test area is pressurized with a specific pressure of $N_2$, the signal increasing as the detector detects the increasing amount of $N_2$ coming from the improperly sealed area. The nut is tightened to eliminate the leak and get back to the system baseline.

Once done, we recorded both pressure and torque, and repeated these steps for many pressure and for the fitting components 70, 80 and 90.

We have found that when a properly cut and shaped tube is being used with a fitting component 90 of the invention provided with a sealing lip in the fitting component detail, the sealing takes place between the lip and the tube. This makes the ferrule sealing a secondary sealing. In fact even with an improper ferrule or improper body internal finish, the fitting component still seals as the ferrule still grips and pushes forward the tube against the sealing lip. In other words, a fitting component provided with a sealing lip advantageously provide two levels of sealing. The first level of sealing is obtained by the contact of the cut extremity of the tube with the sealing lip, and a second level of sealing is obtained by the contact of the ferrule with the inside wall of the fitting component's body. Thanks to these two levels of sealing, the operational lifetime of the fitting component is increased. Indeed, over time, the numerous assembly/disassembly procedures will tend to affect the sealing of the tube with the lip, compromising the first level of sealing. However, thanks to the contact of the ferrule with the inside wall of the fitting component, this second level of sealing will maintain the fluid-tightness/sealing properties of the fitting component assembly.

In summary, and with reference to FIGS. 10 to 16A, the ferrule 38a, 38b, the fitting components 40, 40' or 40", and the combination of the fitting components with the ferrules and/or the threaded nuts advantageously allows to reduce or eliminate torque related problems (ferrule rotation and twisting), allows to reduce the dead volume in the fitting component, provides improved sealing and increases the number of times the fitting component assembly can be disassembled and reassembled. It will be understood by one skilled in the art that a ferrule having characteristics such as those described above could be used with a different fitting component, and that the fitting component described herein could be used with different ferrule.

While the description often refers to a gas chromatography system, the components (ferrule, fitting component and fitting component assembly) of the present invention could be used with any type of systems requiring a connection between two tubes.

Of course, numerous modifications could be made to any of the embodiments described above.

The invention claimed is:

1. A fitting component for receiving a tube, said tube having an inner diameter, an outer diameter and a tube end inserted through a ferrule, a portion of the tube end extending beyond the ferrule being referred to as a pilot, said fitting component comprising:
   a body having first and second extremities, the body including:
      a cavity for receiving the tube end and the ferrule, the cavity being defined by an inner lateral wall and opening on the first extremity of the body, the cavity including a pilot receiving section for receiving the pilot; and
      a channel connecting the cavity to an other portion of the body, the channel having a cross-section smaller than a cross-section of the pilot receiving section;
   a radial annular flange located at an interface of the pilot receiving section with the channel, said flange having an annular sealing lip protruding towards the cavity, the sealing lip being for forming a seal with a radial surface of the pilot, wherein the annular sealing lip is coated with an inert substance softer than the fitting component.

2. The fitting component according to claim 1, wherein the inert substance is gold.

3. The fitting component according to claim 1, wherein the cross-section of the channel corresponds to the inner diameter of the tube.

4. The fitting component according to claim 1, wherein the cavity comprises:

a tapered ferrule receiving section located next to the pilot receiving section; and a threaded nut receiving section opening on the first extremity.

5. The fitting component according to claim 4, in combination with the ferrule, said ferrule being for gripping the tube end and for being compressed at least partially within the tapered ferrule receiving section of the first cavity, said ferrule comprising a front and a rear portion, said front portion having a tapered outer surface coated with an inert substance softer than the fitting component.

6. The fitting component in combination with the ferrule according to claim 5, wherein the inert substance coating the ferrule is gold.

7. The fitting component in combination with the ferrule according to claim 5, wherein the rear portion of the ferrule devised to be in contact with a compression nut is uncoated.

8. The fitting component in combination with the ferrule according to claim 5, wherein the front portion of the ferrule has a sharp edge for gripping the tube.

9. The fitting component in combination with the ferrule according to claim 5, wherein the ferrule has a ferrule central axis and the front portion of the ferrule forms an angle with the ferrule central axis varying between 13 and 16 degrees.

10. The fitting component according to according to claim 4, wherein the fitting component has a fitting component central axis going through the cavity, the tapered ferrule receiving section of the cavity forming an angle with the fitting component central axis varying between 18 and 20 degrees.

11. The fitting component according to claim 4, in combination with a nut having threads and a central bore for passing the tube end through said nut, when in use said nut is screwed within the threaded nut receiving section of the fitting component for compressing the ferrule against a portion of the inner lateral wall forming the tapered ferrule receiving section, the threads of the nut being provided with a lubricant.

12. The fitting component in combination with the nut according to claim 11, wherein a front surface of the nut is also provided with a lubricant.

13. The fitting component in combination with the nut according to claim 11, wherein the lubricant is molybdenum disulfide.

14. The fitting component in combination with the nut according to claim 11, wherein a pitch between each of the threads of the nut is of less than 1/32".

15. The fitting component according to claim 1, wherein said other portion of the fitting component is one of:
a cap for capping the tube end;
a second tube for connection to another device; and
a second cavity for receiving a device and for joining the tube to said device, the cavity defined in claim 1 being a first cavity, the channel connecting the first and the second cavities.

16. The fitting component according to claim 1, wherein:
said cavity and said tube defined in claim 1 are a first cavity and a first tube, respectively;
said other portion of the fitting component includes a second cavity comprising a pilot receiving section, a tapered ferrule receiving section, a threaded nut receiving section and a radial annular flange located at an interface of the pilot receiving section of the second cavity with the channel, said flange having an annular sealing lip protruding towards the second cavity, said channel connecting the first and the second cavities;
the second cavity is for receiving a second tube inserted through a ferrule and a threaded nut, the sealing lip of the flange of the second cavity being for forming a seal with a radial surface of the second tube,
the fitting component thereby allowing to join the first and the second tube.

17. The fitting component according to claim 16, wherein the first and second cavities are identical.

18. A fitting component kit for joining first and second tubes, said tubes having respective outer diameter and tube ends, said fitting component kit comprising:
a fitting component;
first and second ferrules;
first and second threaded nuts;
said first and second ferrules and said first and second threaded nuts being for insertion around the tube ends of the first and second tubes, respectively,
the first and second ferrules being located frontward of the first and second threaded nuts, respectively,
portions of the tube ends extending beyond the ferrules being referred to as pilots,
said fitting component comprising:
a body having first and second extremities;
a bore extending from the first extremity to the second extremity, the bore including:
first and second cavities respectively opening of the first and second extremities of the body and a channel connecting the first and the second cavities,
the first and second cavities for respectively receiving the first and the second tubes, each of said cavities comprising:
a pilot receiving section;
a tapered ferrule receiving section located next to the pilot receiving section; and
a threaded nut receiving section opening on a given one of the extremities;
a radial annular flange located at an interface of the pilot receiving section with the channel, said flange having an annular sealing lip protruding towards a corresponding one of the cavities, the sealing lip being for forming a seal with a radial surface of a corresponding one of the pilots;
each of said ferrules having an outer surface coated with an inert substance softer than the fitting component;
each of said threaded nuts having a front surface and threads coated with a lubricant, wherein for each of the cavities, the annular sealing lip is coated with an inert substance softer than the fitting component.

19. The kit according to claim 18, wherein threads of each of the nuts are spaced by less than 1/32".

* * * * *